United States Patent
Ouderkirk et al.

(10) Patent No.: US 11,245,065 B1
(45) Date of Patent: Feb. 8, 2022

(54) ELECTROACTIVE POLYMER DEVICES, SYSTEMS, AND METHODS

(71) Applicant: Facebook Technologies, LLC, Menlo Park, CA (US)

(72) Inventors: Andrew John Ouderkirk, Redmond, WA (US); Katherine Marie Smyth, Seattle, WA (US)

(73) Assignee: Facebook Technologies, LLC, Menlo Park, CA (US)

( * ) Notice: Subject to any disclaimer, the term of this patent is extended or adjusted under 35 U.S.C. 154(b) by 777 days.

(21) Appl. No.: 16/035,562

(22) Filed: Jul. 13, 2018

Related U.S. Application Data

(60) Provisional application No. 62/646,900, filed on Mar. 22, 2018, provisional application No. 62/650,254, filed on Mar. 29, 2018.

(51) Int. Cl.
| | |
|---|---|
| *H01L 41/193* | (2006.01) |
| *H01L 41/09* | (2006.01) |
| *H01L 41/293* | (2013.01) |
| *H01L 41/047* | (2006.01) |

(52) U.S. Cl.
CPC ...... *H01L 41/0986* (2013.01); *H01L 41/0472* (2013.01); *H01L 41/193* (2013.01); *H01L 41/293* (2013.01)

(58) Field of Classification Search
CPC .............. H01L 41/193; H01L 41/0472; H01L 41/0986; H02N 1/00
See application file for complete search history.

(56) References Cited

U.S. PATENT DOCUMENTS

| | | | |
|---|---|---|---|
| 60,109 | A | 11/1866 | Woodward |
| 3,571,555 | A | 3/1971 | Townes et al. |
| 3,797,922 | A | 3/1974 | Plummer |
| 4,477,158 | A | 10/1984 | Pollock et al. |
| 5,154,862 | A | 10/1992 | Reagan et al. |
| 5,225,244 | A | 7/1993 | Aharoni et al. |
| 5,663,779 | A | 9/1997 | Karasawa |
| 5,956,183 | A | 9/1999 | Epstein et al. |
| 6,081,388 | A | 6/2000 | Widl |

(Continued)

FOREIGN PATENT DOCUMENTS

| | | |
|---|---|---|
| KR | 10-2011-0107812 A | 10/2011 |
| WO | 2008/156166 A1 | 12/2008 |

(Continued)

OTHER PUBLICATIONS

Adaptive glasses, http://tvc.utah.edu, as accessed on Mar. 13, 2018.

(Continued)

*Primary Examiner* — J. San Martin
(74) *Attorney, Agent, or Firm* — FisherBroyles, LLP

(57) ABSTRACT

An electroactive device may include (1) an electroactive polymer element having a first surface and a second surface opposing the first surface, (2) a primary electrode abutting the first surface, and (3) a secondary electrode abutting the second surface. The electroactive polymer element may be transformed from an initial state to a deformed state and may achieve substantially uniform strain by the application of an electrostatic field produced by a potential difference between the electrodes. Various other devices, systems, and methods are also disclosed.

20 Claims, 17 Drawing Sheets

(56) References Cited

U.S. PATENT DOCUMENTS

| | | |
|---|---|---|
| 6,420,441 B1 | 7/2002 | Allen et al. |
| 7,008,054 B1 | 3/2006 | Kurtin et al. |
| 7,118,219 B2 | 10/2006 | Itagaki |
| 7,864,440 B2 | 1/2011 | Berge |
| 7,866,816 B2 | 1/2011 | Kurtin |
| 8,210,678 B1 | 7/2012 | Farwig |
| 8,441,737 B2 | 5/2013 | Buch et al. |
| 10,409,089 B2 | 9/2019 | Pugh et al. |
| 10,698,224 B1 | 6/2020 | Cooke et al. |
| 10,754,145 B1 | 8/2020 | Ouderkirk et al. |
| 10,881,287 B1 | 1/2021 | Ouderkirk et al. |
| 10,928,558 B1 | 2/2021 | Cooke et al. |
| 10,928,656 B1 | 2/2021 | Smyth et al. |
| 10,962,791 B1 | 3/2021 | Ouderkirk et al. |
| 11,011,739 B1 | 5/2021 | Ouderkirk et al. |
| 11,048,075 B1 | 6/2021 | Ouderkirk et al. |
| 2003/0003295 A1 | 1/2003 | Dreher et al. |
| 2003/0054115 A1 | 3/2003 | Albano et al. |
| 2003/0067245 A1* | 4/2003 | Pelrine .................. H01L 41/042 310/311 |
| 2003/0083433 A1 | 5/2003 | James et al. |
| 2006/0024976 A1 | 2/2006 | Waldfried et al. |
| 2008/0049431 A1 | 2/2008 | Boek et al. |
| 2008/0088793 A1 | 4/2008 | Sverdrup et al. |
| 2008/0123049 A1 | 5/2008 | Volk |
| 2008/0144185 A1 | 6/2008 | Wang et al. |
| 2008/0170299 A1 | 7/2008 | Kawabata |
| 2008/0171431 A1 | 7/2008 | Yu et al. |
| 2008/0290435 A1 | 11/2008 | Oliver et al. |
| 2008/0291394 A1 | 11/2008 | Ishak |
| 2009/0015786 A1 | 1/2009 | Harris |
| 2009/0027778 A1 | 1/2009 | Wu et al. |
| 2009/0096106 A1 | 4/2009 | Vrtis et al. |
| 2009/0289529 A1* | 11/2009 | Ito ....................... H01L 41/1132 310/365 |
| 2009/0304924 A1 | 12/2009 | Gadgil |
| 2010/0075056 A1 | 3/2010 | Axisa et al. |
| 2010/0109486 A1* | 5/2010 | Polyakov ............ H01L 41/0475 310/365 |
| 2010/0168409 A1 | 7/2010 | Fujita |
| 2010/0202054 A1 | 8/2010 | Niederer |
| 2010/0238400 A1 | 9/2010 | Volk |
| 2011/0075096 A1 | 3/2011 | Ishak et al. |
| 2011/0085131 A1 | 4/2011 | Gupta et al. |
| 2011/0176105 A1 | 7/2011 | Harris |
| 2011/0179861 A1 | 7/2011 | Grange et al. |
| 2011/0235326 A1 | 9/2011 | Yeh et al. |
| 2011/0294305 A1 | 12/2011 | Jacobs et al. |
| 2012/0029416 A1 | 2/2012 | Parker et al. |
| 2012/0032559 A1* | 2/2012 | Hino ..................... H01L 41/047 310/331 |
| 2012/0041553 A1 | 2/2012 | Gupta et al. |
| 2012/0044571 A1 | 2/2012 | Mukawa |
| 2012/0087015 A1 | 4/2012 | Nibauer et al. |
| 2012/0092775 A1 | 4/2012 | Duston et al. |
| 2012/0170920 A1 | 7/2012 | Moreau et al. |
| 2012/0229754 A1 | 9/2012 | Iyer et al. |
| 2012/0250151 A1 | 10/2012 | Lee et al. |
| 2012/0287512 A1 | 11/2012 | Egan et al. |
| 2013/0171546 A1 | 7/2013 | White et al. |
| 2013/0176628 A1 | 7/2013 | Batchko et al. |
| 2013/0300635 A1 | 11/2013 | White et al. |
| 2014/0009039 A1 | 1/2014 | Jenninger et al. |
| 2014/0153102 A1 | 6/2014 | Chang |
| 2014/0300857 A1 | 10/2014 | Cohen-Tannoudji et al. |
| 2014/0312737 A1 | 10/2014 | Jenninger et al. |
| 2015/0062719 A1 | 3/2015 | Kyung et al. |
| 2015/0116656 A1 | 4/2015 | Stevens et al. |
| 2015/0138110 A1 | 5/2015 | Yairi et al. |
| 2015/0146161 A1 | 5/2015 | Rigato et al. |
| 2015/0302990 A1 | 10/2015 | Ghosh et al. |
| 2015/0323812 A1 | 11/2015 | Ishak et al. |
| 2016/0004099 A1 | 1/2016 | Steven et al. |
| 2016/0091635 A1 | 3/2016 | Ibuki et al. |
| 2016/0187985 A1 | 6/2016 | Lim et al. |
| 2017/0045649 A1 | 2/2017 | Bolis |
| 2017/0160600 A1 | 6/2017 | Galstian et al. |
| 2017/0177106 A1* | 6/2017 | Kihara ............... H03K 17/9643 |
| 2017/0184848 A1 | 6/2017 | Vallius |
| 2017/0188021 A1 | 6/2017 | Lo et al. |
| 2017/0192595 A1 | 7/2017 | Choi et al. |
| 2017/0261653 A1 | 9/2017 | Peyman |
| 2017/0299956 A1 | 10/2017 | Holland et al. |
| 2017/0317269 A1 | 11/2017 | Zhang et al. |
| 2017/0336641 A1 | 11/2017 | Von Und Zu Liechtenstein |
| 2018/0255250 A1 | 9/2018 | Price et al. |
| 2018/0275394 A1 | 9/2018 | Yeoh et al. |
| 2018/0335649 A1 | 11/2018 | Tsai |
| 2019/0243123 A1 | 8/2019 | Bohn |
| 2019/0296218 A1 | 9/2019 | Ouderkirk et al. |
| 2019/0302479 A1 | 10/2019 | Smyth et al. |
| 2020/0166742 A1 | 5/2020 | Peyman |

FOREIGN PATENT DOCUMENTS

| | | |
|---|---|---|
| WO | 2010/078666 A1 | 7/2010 |
| WO | 2010/104904 A2 | 9/2010 |
| WO | 2019/183431 A1 | 9/2019 |
| WO | 2019/190887 A1 | 10/2019 |

OTHER PUBLICATIONS

Billah et al., Microstructure Evolution and Electrical Characterization of Lanthanum doped Barium Titanate (BaTiO3) Ceramics, Int'l Conference on Mechanical Engineering, AIP Conf. Proc. 1754, 030006-1-030006-7 (Jul. 12, 2016).

Cao et al., Grain Size and Domain Size Relations in Bulk Ceramic Ferroelectric Materials, J. Phys. Chem Solids vol. 57, No. 10, pp. 1499-1505, 1996.

Ding et al., "Surface profiling of an aspherical liquid lens with a varied thickness membrane," Optics Express 3122-3132, vol. 25, No. 4 (Feb. 6, 2017).

He et al., Linear Electro-Optic Properties of Orthorhombic PZN-8%PT Single Crystal, IEEE Transactions on Ultrasonics, Ferroelectrics, and Frequency Control, vol. 58, No. 6 (Jun. 1, 2011).

http://glidewelldental.com/education/inclusive-dental-implant-magazine-volume-2-issue-4/, as accessed on Jun. 12, 2018.

http://www.optotune.com/technology/focus-tunable-lenses, as accessed on Mar. 13, 2018.

http://www.polight.com/technology-and-products/how-does-it-work/default.aspx, as accessed on Mar. 13, 2018.

https://adlens.com/how-it-works/, as accessed on Mar. 28, 2018.

https://www.piceramic.com/en/piezo-technology/picma/, as accessed on Mar. 14, 2018.

https://www.piceramic.com/en/piezo-technology/properties-piezo-actuators/displacement-modes/, as accessed on Mar. 14, 2018.

Jiang et al., Transparent Electro-Optic Ceramics and Devices, Optoelectronic devices and integration, pts 1 and 2; SPIE-Int Soc Optical Engineering, Bellingham, pp. 380-394 (Jan. 17, 2005).

Keplinger et al., Stretchable, Transparent, Ionic Conductors, Science Magazine, vol. 341, pp. 984-987 (Aug. 30, 2013).

Kong et al., Transparent Ceramics, Topics in Mining, Metallurgy, and Materials Engineering, Ch. 2: Transparent Ceramic Materials, pp. 29-91 (2015).

Patra et al., Comparison on Optical Properties of Pure and Doped Lithium Tetraborate Single Crystals and Glasses, Solid State Physics: Proceedings of the 56th DAE Solid State Physics Symposium 2011, AIP Conf. Proc. 1447, 1335-46 (Dec. 11, 2012).

Riegler et al., Index Matching Silicone for High Brightness LED Packaging (Mar. 18, 2005).

Shian et al., Tunable Lenses using Transparent Dielectric Elastomer Actuators, Optics Express, vol. 21, No. 7 (Apr. 2, 2013).

The effect of slip on the motion of a sphere close to a wall and of two adjacent spheres, L. M. Hocking (Jul. 1, 1973).

Wang et al., A Highly Stretchable, Transparent, and Conductive Polymer, Sci. Adv. 2017; 3:e1602076 (Mar. 10, 2017).

www.americanpiezo.com/knowledge-center/piezo-theory/new-materials/html, as accessed on Mar. 15, 2018.

(56) References Cited

OTHER PUBLICATIONS

Zhao et al., "Spherical aberration free liquid-filled tunable lens with variable thickness membrane," Optics Express 21264-21278, vol. 23, No. 16. (Aug. 5, 2015).
Andrew J. Ouderkirk, et al.; Apparatuses, Systems, and Methods for Adjusting Fluid Lenses; U.S. Appl. No. 16/008,635, filed Jun. 14, 2018.
Katherine Marie Smyth, et al.; Optical Lens Assemblies, Head-Mounted Displays, and Related Methods; U.S. Appl. No. 16/021,650, filed Jun. 28, 2018.
Andrew John Ouderkirk, et al.; Multi-Element Prescription Lenses With Eye-Tracking; U.S. Appl. No. 16/041,634, filed Jul. 20, 2018.
Andrew John Ouderkirk, et al.; Electroactive Polymer Devices and Nanovoided Polymer Materials and Methods and Systems for Fabrication Thereof; U.S. Appl. No. 16/106,945, filed Aug. 21, 201.
Andrew John Ouderkirk, et al.; Nanovoided Electroactive Polymer Devices, Systems, and Methods; U.S. Appl. No. 16/041,858, filed Jul. 23, 2018.
Andrew John Ouderkirk, et al.; Electroactive Polymer Devices, Systems, and Methods; U.S. Appl. No. 16/059,091, filed Aug. 9, 2018.
Andrew John Ouderkirk, et al.; Optical Devices, Systems, and Methods of Manufacturing; U.S. Appl. No. 62/646,900, filed Mar. 22, 2018.
Andrew John Ouderkirk, et al.; Optical Devices, Systems, and Methods of Manufacturing; U.S. Appl. No. 62/650,254, filed Mar. 29, 2018.
Katherine Marie Smyth, et al.; Optical Lens Assemblies and Related Methods; U.S. Appl. No. 16/018,746, filed Jun. 26, 2018.
Katherine Marie Smyth, et al.; Systems and Methods for Actuation of Asymmetric Optical Elements; U.S. Appl. No. 15/992,731, filed May 30, 2018.
Andrew John Ouderkirk, et al.; Optical Lens Assemblies and Related Methods; U.S. Appl. No. 16/018,752, filed Jun. 26, 2018.
John M. Cooke, et al.; Optical Lens Assemblies, Head-Mounted Displays, and Methods of Altering Optical Properties of Optical Lens Assemblies; U.S. Appl. No. 16/013,837, filed Jun. 20, 2018.
Katherine Marie Smyth, et al.; Optical Lens Assemblies, Head-Mounted Displays, and Related Methods; U.S. Appl. No. 16/016,428, filed Jun. 22, 2018.
John M. Cooke, et al.; Optical Lens Assemblies, Head-Mounted Displays, and Related Methods; U.S. Appl. No. 16/021,580, filed Jun. 28, 2018.
Notice of Allowance received for U.S. Appl. No. 15/972,794 dated Oct. 16, 2020, 22 pages.
Notice of Allowance received for U.S. Appl. No. 15/992,731 dated Nov. 18, 2020, 37 pages.
Final Office Action received for U.S. Appl. No. 16/106,945 dated Nov. 24, 2020, 94 pages.
Final Office Action received for U.S. Appl. No. 16/018,752 dated Nov. 30, 2020, 41 pages.
Notice of Allowance received for U.S. Appl. No. 16/018,746 dated Nov. 3, 2020, 39 pages.
Notice of Allowance received for U.S. Appl. No. 16/021,580 dated Dec. 9, 2020, 68 pages.
Preinterview First Office Action received for U.S. Appl. No. 16/021,650 dated Feb. 1, 2021, 47 pages.
Gurvich, Mark R., "On Characterization of Anisotropic Elastomeric Materials for Structural Analysis", Rubber Chemistry and Technology, vol. 77, No. 1, 2004, pp. 115-130.
Non-Final Office Action received for U.S. Appl. No. 16/106,945 dated Mar. 30, 2021, 111 pages.
Notice of Allowance received for U.S. Appl. No. 16/018,752 dated Mar. 10, 2021, 32 pages.
Communication pursuant to Article 94(3) EPC received for EP Patent Application Serial No. 19715707.6 dated Mar. 22, 2021, 5 page.
Non-Final Office Action received for U.S. Appl. No. 16/016,428 dated Mar. 12, 2021, 56 pages.
Non-Final Office Action received for U.S. Appl. No. 16/013,837 dated Jan. 23, 2020, 22 pages.
Notice of Allowance received for U.S. Appl. No. 16/013,837 dated Apr. 14, 2020, 14 pages.
Preinterview First Office Action received for U.S. Appl. No. 15/992,731 dated Sep. 27, 2019, 17 pages.
Final Office Action received for U.S. Appl. No. 15/992,731 dated Jun. 2, 2020, 25 pages.
Non-Final Office Action received for U.S. Appl. No. 15/992,731 dated Aug. 24, 2020, 27 pages.
Examiner-Initiated Interview Summary received for U.S. Appl. No. 16/008,635 dated Apr. 20, 2020, 3 pages.
Notice of Allowance received for U.S. Appl. No. 16/008,635 dated May 4, 2020, 32 pages.
Non-Final Office Action received for U.S. Appl. No. 16/059,091 dated Apr. 8, 2020, 54 pages.
Final Office Action received for U.S. Appl. No. 16/059,091 dated Sep. 21, 2020, 18 pages.
Non-Final Office Action received for U.S. Appl. No. 16/106,945 dated Apr. 16, 2020, 59 pages.
Non-Final Office Action received for U.S. Appl. No. 16/041,634 dated Jul. 30, 2020, 24 pages.
Notice of Allowance received for U.S. Appl. No. 16/041,634 dated Aug. 28, 2020, 31 pages.
Preinterview First Office Action received for U.S. Appl. No. 16/018,752 dated Dec. 16, 2019, 19 pages.
Preinterview First Office Action received for U.S. Appl. No. 16/018,746 dated Jul. 14, 2020, 20 pages.
Notice of Allowance Action received for U.S. Appl. No. 16/018,746 dated Sep. 17, 2020, 24 pages.
Preinterview First Office Action received for U.S. Appl. No. 16/021,580 dated Aug. 4, 2020, 48 pages.
"Adjustable Reading Glasses," URL: https://adlens.com/, retrieved on May 7, 2018, 1 page.
Guha et al., "Creating nanoscale emulsions using condensation", Nature Communications, vol. 8, No. 1371, Nov. 2017, pp. 1-7.
Merriam-Webster, "Porosity", URL: https://www.merriam-webster.com/dictionary/porosity, retrieved on Apr. 8, 2020, pp. 1-8.
International Search Report and Written Opinion received for PCT Application Serial No. PCT/US2019/023484 dated Jul. 3, 2019, 9 pages.
International Preliminary Report on Patentability received for PCT Application Serial No. PCT/US2019/023484 dated Oct. 1, 2020, 8 pages.
International Search Report and Written Opinion received for PCT Application Serial No. PCT/US2019/023485 dated Jul. 4, 2019, 11 pages.
International Preliminary Report on Patentability received for PCT Application Serial No. PCT/US2019/023485 dated Oct. 8, 2020, 8 pages.
Non-Final Office Action received for U.S. Appl. No. 16/016,428 dated Jun. 16, 2021, 43 pages.

* cited by examiner

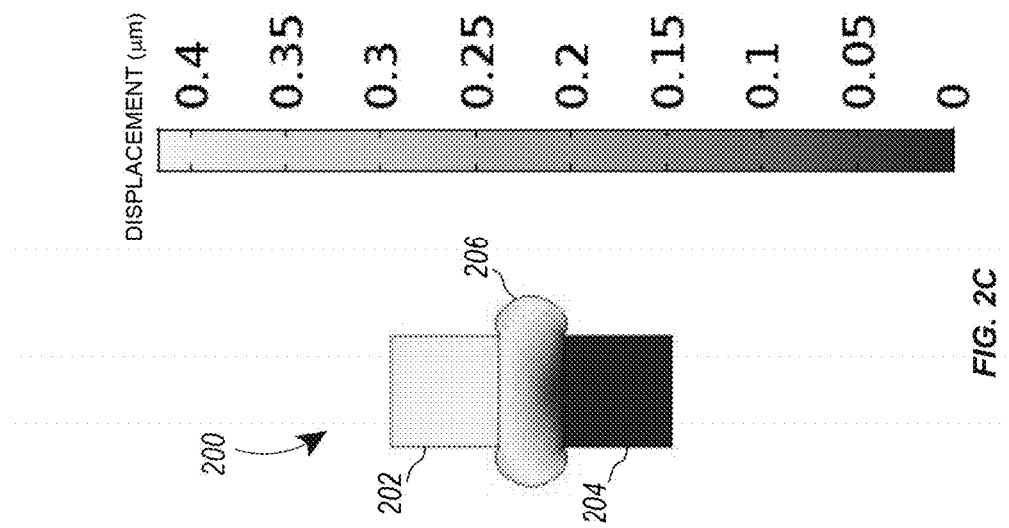
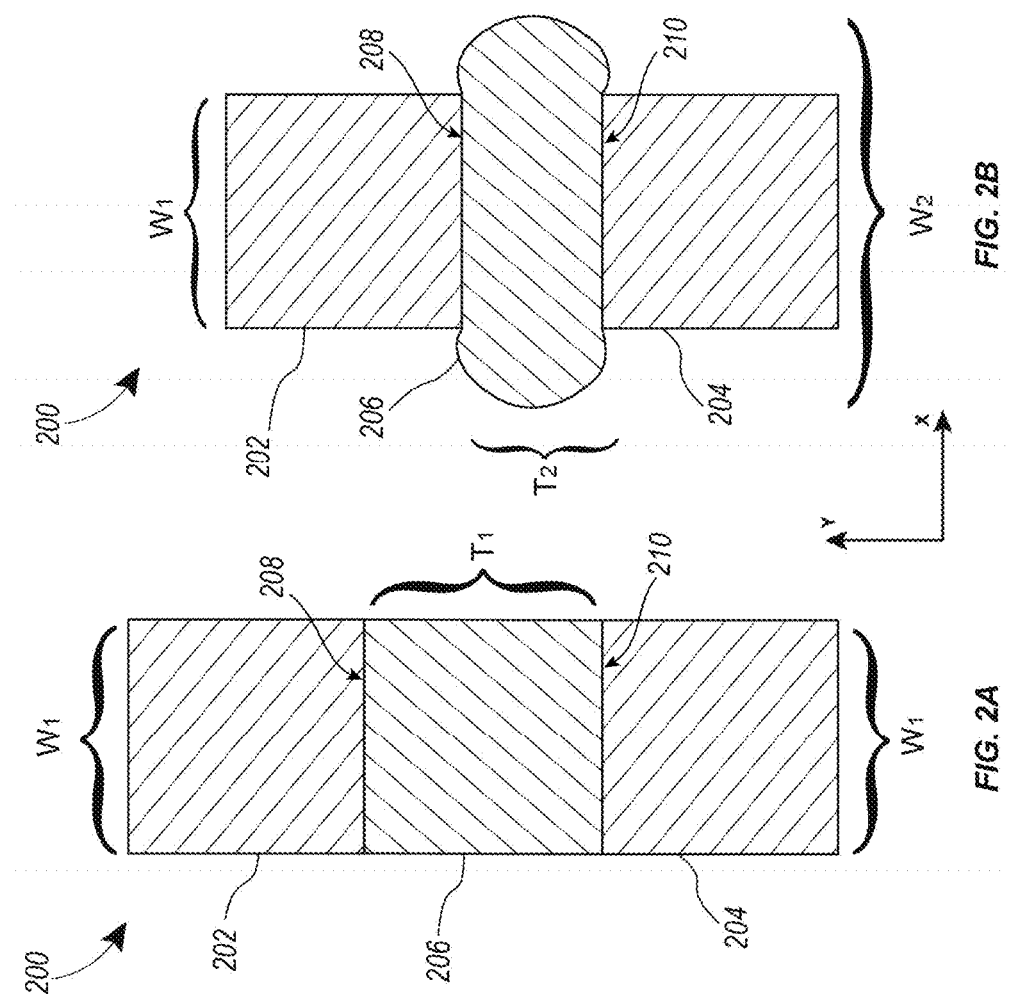
FIG. 2A
FIG. 2B
FIG. 2C

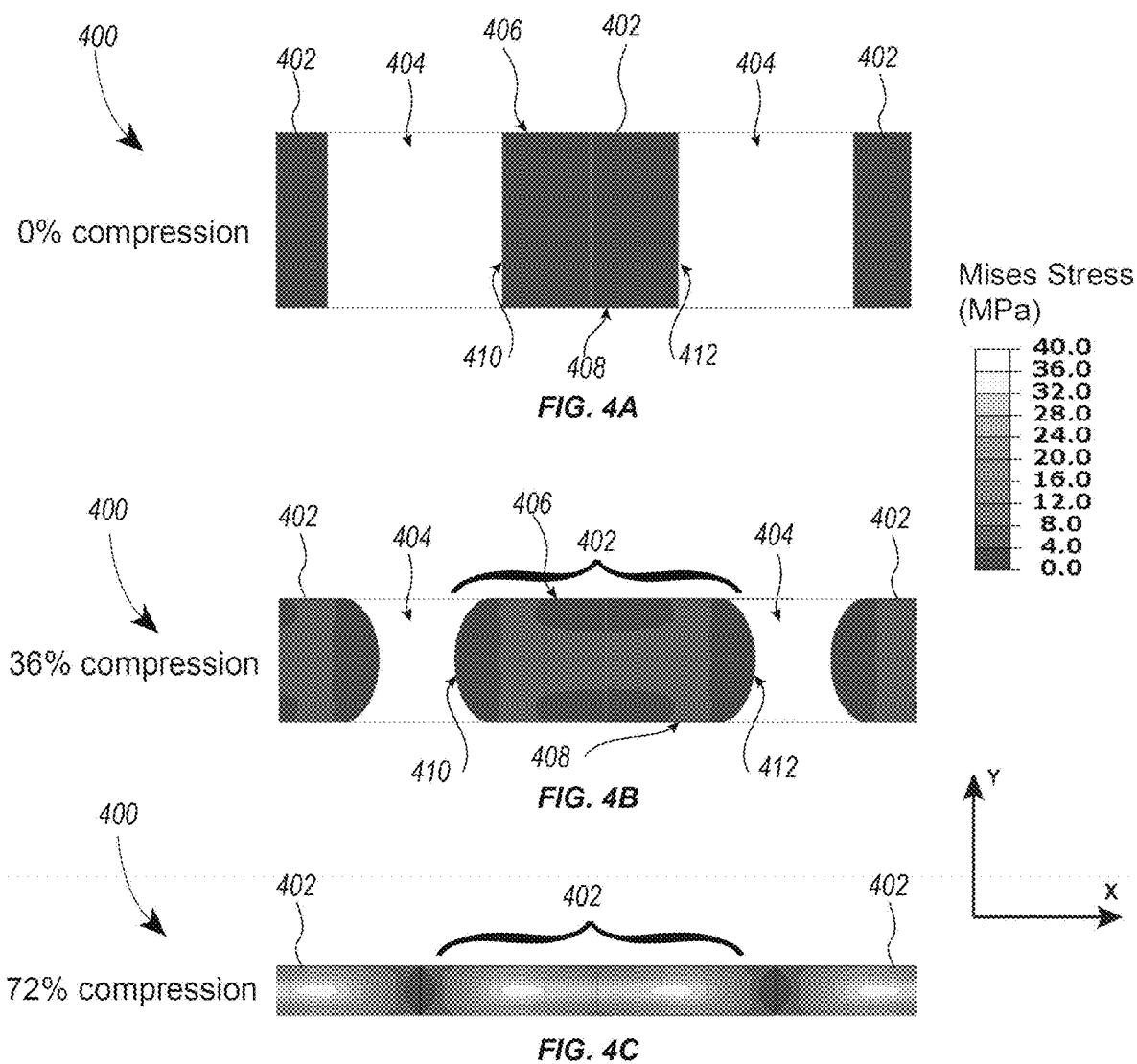

ELECTROACTIVE POLYMER DEVICES, SYSTEMS, AND METHODS

CROSS REFERENCE TO RELATED APPLICATION

This application is a non-provisional utility application which claims the benefit of U.S. Provisional Application No. 62/646,900 filed 22 Mar. 2018, and U.S. Provisional Application No. 62/650,254 filed 29 Mar. 2018, the disclosures of each of which are incorporated, in their entirety, by this reference.

BACKGROUND

Electroactive polymer (EAP) materials include materials that may change their shape in the presence of an electric field, thus exhibiting electromechanical coupling. There are several conventional subspecies of these materials such as electrostrictive polymers, piezoelectric polymers, and dielectric polymers. A common EAP is a dielectric elastomer. A separate category of EAPs may include those that change their shapes due to intermolecular ion transactions. While EAP materials may be functionally similar to piezoelectric materials in some respects, EAP materials may exhibit considerably different electromechanical response characteristics.

EAP materials have been investigated for use in various technologies, including actuation and/or energy harvesting applications. Unfortunately, the energy density and, in some applications, the specific power density of electroactive polymers in practical devices are commonly considerably lower than for other materials, such as lead-containing PZT and its variations. Thus, there is a need for increasing both the energy density and specific power density of electroactive devices.

SUMMARY

As will be described in greater detail below, the instant disclosure describes apparatuses, systems, and methods for the design and manufacture of electroactive devices that are able to achieve essentially uniform strain. For example, an electroactive device may include (1) an electroactive polymer element having a first surface and a second surface opposing the first surface, (2) a primary electrode abutting the first surface, and (3) a secondary electrode abutting the second surface. The electroactive polymer element may be transformed from an initial state to a deformed state and may achieve substantially uniform strain by application of an electrostatic field produced by a potential difference between the primary electrode and the secondary electrode.

In some embodiments, the deformed state of the electroactive polymer element may be a compressed state and a direction of maximum compression of the electroactive polymer element may be one substantially parallel to the electrostatic field. An amount of deformation of the electroactive polymer element in the deformed state may correspond to a strength of the electrostatic field. In at least one example, the electroactive polymer element may have a maximum thickness in an undeformed state and a minimum thickness in a maximally deformed state when an electrostatic field strength of at least a certain value is applied. In this example, a ratio of the maximum thickness to the minimum thickness may be from approximately 2:1 to approximately 5:1.

According to various embodiments, a ratio of the maximum thickness to a width of the electroactive polymer element in the undeformed state may be from approximately 2:1 to approximately 1:5. In at least one example, the maximum thickness of the electroactive polymer element may be from approximately 100 nm to approximately 10 µm. A width of the electroactive polymer element in the undeformed state may be from approximately 100 nm to approximately 100 µm. The electroactive polymer element may include at least one of a dielectric polymer material or an elastomeric polymer material.

According to at least one embodiment, the electroactive device may include a dielectric material disposed between the electroactive polymer element and at least one of the primary electrode or the secondary electrode. In this example, the dielectric material may have a dielectric constant of between approximately 2 and approximately 30. At least one of the primary electrode or the secondary electrode may be a movable electrode that is movable in conjunction with displacement of an abutting surface portion of the electroactive polymer element. In at least one embodiment, at least one of the primary electrode or the secondary electrode may be a movable electrode that is movable in conjunction with displacement of an abutting surface portion of the electroactive polymer element. In this example, one of the primary electrode or the secondary electrode may be the movable electrode and the other of the primary electrode or the secondary electrode may be a fixed electrode that holds another abutting surface portion of the electroactive polymer element in a fixed position.

In some embodiments, the electroactive polymer element may further include a third surface extending between the first surface and the second surface. The third surface may extend at an oblique angle relative to at least one of the first surface or the second surface when the electroactive polymer element is in an undeformed state. In various examples, the electroactive polymer element may have a quadrilateral cross-sectional profile formed by a third surface extending between the first surface and the second surface. In this example, an interior angle that is formed between the third surface and a direction of the electrostatic field between the primary electrode and the secondary electrode may be between 0 and approximately 70 degrees when the electroactive polymer element is in an undeformed state. According to at least one example, the electroactive device may include at least one electroactive actuator. In some examples, the electroactive polymer element may be doped with barium titanate ranging in fractional composition by volume from approximately 1% to approximately 70%.

According to various embodiments, an electroactive device may include (1) a set of paired electrodes that includes a first set of electrodes and a second set of electrodes, each electrode of the second set of electrodes being paired with an opposing electrode of the first set of electrodes, and (2) an array of electroactive polymer elements separated by interstitial volumes. In this example, each electroactive polymer element of the array of electroactive polymer elements may be disposed between the opposing electrodes of a paired electrode and an electrostatic field generated by each of the paired electrodes may cause each electroactive polymer element disposed therebetween to deform from an initial state to a deformed state according to a strength of the electrostatic field.

In some embodiments, a first pair of opposing electrodes may produce a different electrostatic field strength than a second pair of opposing electrodes. In at least one example, each electroactive polymer element of the array of electroactive polymer elements may extend in an elongation direction approximately transverse to lines of an electrostatic field, the elongation directions of the array of electroactive polymer elements being approximately parallel to one another. Each of the electroactive polymer elements in the deformed state may be expanded in dimensions approximately transverse to a direction of the electrostatic field between the corresponding paired electrodes to infill at least partially at least one interstitial volume.

A corresponding method may include (1) abutting a primary electrode on a first surface of an electroactive polymer element, and (2) abutting a secondary electrode on a second surface of the electroactive polymer element, the second surface opposing the first surface. The electroactive polymer element may be deformable from an initial state to a deformed state in the presence of an electrostatic field produced by a potential difference between the primary electrode and the secondary electrode such that the electroactive polymer element experiences substantially uniform strain.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

FIGS. 2A-2C are cross-sectional views of an exemplary electroactive device according to at least one embodiment.

FIGS. 4A-4C are cross-sectional views of an exemplary electroactive device structure that includes an array of EAP elements in accordance with some embodiments.

Figure 1:
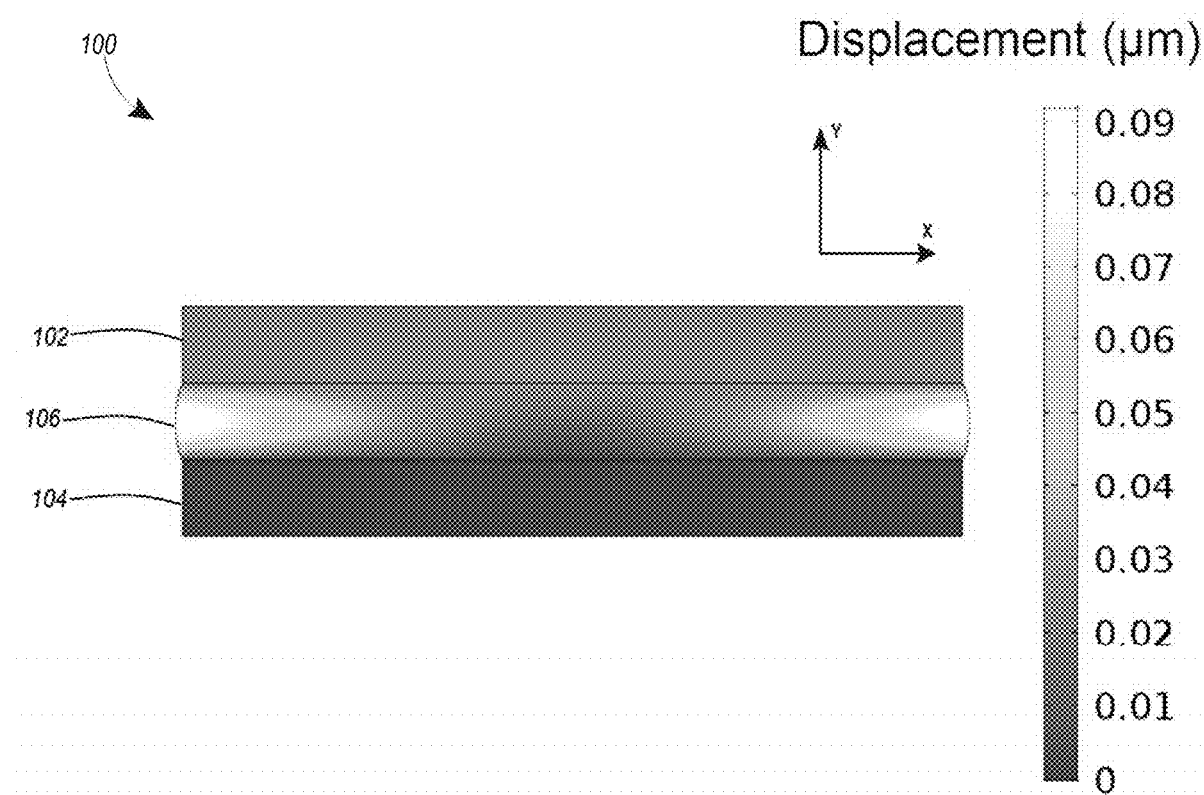
FIG. 1 is a cross-sectional view of an electroactive device.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

As will be described in greater detail below, the instant disclosure describes various electroactive devices, systems, and corresponding methods. As will be described in greater detail below, embodiments of the instant disclosure may include an electroactive device having an electroactive polymer element with a first surface and a second surface opposing the first surface. The electroactive device may also include paired electrodes, such as a primary electrode abutting the first surface of the electroactive polymer element and a secondary electrode abutting the second surface of the electroactive polymer element. The electroactive polymer element may be deformable from an undeformed state or partially deformed state to a more fully deformed state, such as a compressed state, when a voltage difference is applied between the primary electrode and the secondary electrode such that the electroactive polymer element experiences substantially uniform strain between the primary electrode and the secondary electrode in the deformed state.

The following will provide, with reference to FIGS. 1, 2, and 4A-6C, examples of electroactive devices. In addition, the discussion corresponding to FIGS. 3 and 7-17 will provide examples of characteristics exhibited by various electroactive devices. Finally, the discussion corresponding to FIG. 18 will provide examples of methods for forming electroactive devices.

According to some embodiments, an electroactive polymer (EAP) may be a deformable polymer material that deforms (e.g., compresses, elongates, bends, etc.) via a force created by an electrostatic field. The EAP may be symmetric with regard to electrical charge (e.g., PDMS, acrylates, etc.) or asymmetric (e.g., poled PVDF or its copolymers such as PVDF:TrFE, etc.). In the presence of an electrostatic field, an EAP may deform according to the strength of that field. Generation of such a field is may be accomplished by placing the EAP between two electrodes, each of which is at a different potential. As the potential difference (i.e., voltage difference) between the electrodes is increased (e.g., from zero potential) the amount of deformation may also increase, principally electric along field lines. This deformation will reach a saturation point when a certain voltage difference has been reached. In the presence of no electrostatic field, the EAP may be in its relaxed state undergoing no induced deformation, or stated equivalently, no induced strain, either internal or external.

The physical origin of the compressive nature of EAP in the presence of an electrostatic field (E-field), being the force created between opposite electric charges, is that of the Maxwell stress, which is expressed mathematically with the Maxwell tensor. The level of strain or deformation induced by a given E-field is dependent on the square of the E-field strength, the dielectric constant of the EAP, and on the elastic compliance of the material in question. Compliance in this case is the change of strain with respect to stress or, equivalently, in more practical terms, the change in displacement with respect to force.

Electroactive devices described herein may be devices that convert electrical energy to mechanical energy and/or devices that convert mechanical energy to electrical. Examples of electroactive devices may include, without limitation, actuators, sensors, microelectromechanical devices, and/or any other suitable devices. In various embodiments, electroactive devices may include paired electrodes, which allow the creation of the electrostatic field that forces constriction of the EAP. Such electrodes may include relatively thin, electrically conductive layers or elements and may be of a non-compliant or compliant nature. Any suitable materials may be utilized in the electrodes, including electrically conductive materials suitable for use in thin-film electrodes, such as, for example, aluminum, transparent conductive oxides, silver, indium, gallium, zinc, carbon nanotubes, carbon black, and/or any other suitable materials formed by vacuum deposition, spray, adhesion, and/or any other suitable technique either on a non-EAP layer or directly on the EAP surface itself. In some embodiments, the electrode or electrode layer may be self-healing, such that damage from local shorting of a circuit can be isolated. Suitable self-healing electrodes include thin films of metals, such as, for example, aluminum having a thickness of about 30 nm.

According to at least one embodiment, an electroactive device may include an EAP element having a first surface and a second surface opposite the first surface. The electroactive device may also include paired electrodes, including a primary electrode abutting (i.e., touching, in physical contact with, adhered to, and/or in close proximity to) the first surface of the EAP element and a secondary electrode abutting the second surface of the EAP element.

EAPs, without external dimensional constraints, may contract along electrostatic E-field lines between abutting electrodes and expand in transverse dimensions. This expansion may cause non-uniformities in strains. Embodiments presented herein may overcome these unwanted deformations and create a substantially uniform E-field-induced strain.

An example of this deficiency outlined above is illustrated in FIG. 1. This figure shows an electroactive device 100 that includes a movable electrode 102 and a fixed electrode 104 that are spaced with an EAP element 106 positioned therebetween. In this example, EAP element 106 in an undeformed state is 1 µm thick along a direction (i.e., along the Y-direction shown in FIG. 1) between movable electrode 102 and fixed electrode 104. In the example shown in FIG. 1, a width (i.e., a width in the X-direction shown in FIG. 1) of each of movable electrode 102, fixed electrode 104, and EAP element 106 in the undeformed state is 10 µm. As shown in FIG. 1, overall displacement of movable electrode 102 in the X-direction requires a substantially larger displacement due to compression of EAP element 106 near the lateral edges of EAP element 106 in comparison to inner portions of EAP element 106 disposed away from the lateral edges when an electrostatic field is generated between movable electrode 102 and fixed electrode 104.

FIGS. 2A-2C show an exemplary electroactive device, such as an electroactive actuator, that may overcome the above-described deficiencies. According to at least one embodiment, an electroactive device may include an EAP element having a first surface and a second surface opposite the first surface. The electroactive device may also include paired electrodes, including a primary electrode abutting the first surface of the EAP element and a secondary electrode abutting the second surface of the EAP element. A ratio of a width $W_1$ (i.e., a width in the X-direction shown in FIG. 2A) of the undeformed EAP element to a thickness (i.e., a thickness in the Y-direction shown in FIG. 2A) of the undeformed EAP element between the paired electrodes may be lower than that illustrated in FIG. 1 such that the EAP element is deformed in a more uniform manner than EAP element 106 of electroactive device 100 illustrated in FIG. 1.

For example, as shown in FIGS. 2A-2C, electroactive device 200 includes a primary electrode 202 and a secondary electrode 204 that are spaced with an EAP element 206 positioned therebetween such that primary electrode 202 abuts a first surface 208 of EAP element 206 and secondary electrode 204 abuts a second surface 210 of EAP element 206 opposite first surface 208. In this example, EAP element 206 in an undeformed state has a thickness $T_1$ of 1 µm in a direction (i.e., in the Y-direction shown in FIG. 2A) between primary electrode 202 and secondary electrode 204. However, in contrast to electroactive device 100 shown in FIG. 1, primary electrode 202, secondary electrode 204, and EAP element 206 of electroactive device 200 shown in FIG. 2A each have a much narrower width $W_1$ of 1 µm. In contrast to electroactive device 100 shown in FIG. 1, the deformation of EAP element 206 of electroactive device 200 is much more uniform throughout, as shown in FIG. 2C. Accordingly, the displacement due to compression of EAP element 206 is similar to the displacement of primary electrode 202 in the X-direction.

In some embodiments, EAP element 206 may be deformable from an undeformed state, as illustrated in FIG. 2A, or a partially deformed state to a more fully deformed state, as illustrated in FIG. 2B, when a voltage difference is applied between primary electrode 202 and secondary electrode 204 such that EAP element 206 experiences substantially uniform strain between primary electrode 202 and secondary electrode 204 in the deformed state. In some examples, the deformed state of EAP element 206 may be a compressed state in which EAP element 206 has a decreased thickness $T_2$ in the Y-direction, as shown in FIG. 2B. Thickness, as used herein, may refer to the extent of at least a portion of an EAP element parallel to an E-field generated between paired electrodes abutting the EAP element. In some examples, the initial state of EAP element 206 may be one already influenced by an E-field generated between primary electrode 202 and secondary electrode 204, and the E-field may be increased to amplify the deformations induced. According to some embodiments, an amount of deformation of EAP element 206 in the deformed state, as shown in FIGS. 2B and 2C, may correspond to the strength of the E-field or, equivalently, an amount of voltage applied between primary electrode 202 and secondary electrode 204. In at least one example, when EAP element 206 is in a compressed state, EAP element may expand laterally (i.e., in the X-direction shown in FIG. 2A) such that EAP element has an increased width $W_2$ in the X-direction, as illustrated in FIG. 2B. For example, as shown in FIG. 2B, EAP element 206 may protrude laterally beyond electrode 202 and/or 204, which may have width $W_1$ in the X-direction. In some embodiments, EAP element 206 may be initially stretched in the X-direction.

EAP element 206 may have a maximum thickness (e.g., thickness $T_1$ shown in FIG. 2A) in an undeformed or relaxed state and a minimum thickness (e.g., thickness $T_2$ shown in FIG. 2B) in a maximally deformed state when a voltage difference of at least a certain value is applied between primary electrode 202 and secondary electrode 204. In some embodiments a ratio of the maximum thickness to the minimum thickness may be from approximately 2:1 to approximately 5:1.

According to at least one embodiment, a ratio of the maximum thickness to a width of EAP element 206 in the undeformed state may be from approximately 2:1 to approximately 1:5 (e.g., approximately 2:1, approximately 1.5:1, approximately 1:1, approximately 1:1.5, approximately 1:2, approximately 1:3, approximately 1:4, approximately 1:5). In at least one example, a maximum thickness of EAP element 206 may be from approximately 100 nm to approximately 10 µm (e.g., approximately 100 nm, approximately 500 nm, approximately 1 µm, approximately 2 µm, approximately 3 µm, approximately 4 µm, approximately 5 µm, approximately 6 µm, approximately 7 µm, approximately 8 µm, approximately 9 µm, approximately 10 µm). Additionally, or alternatively, a width of EAP element 206 in the undeformed state may be from approximately 100 nm to approximately 100 µm (e.g., approximately 100 nm, approximately 500 nm, approximately 1 µm, approximately 10 µm, approximately 20 µm, approximately 30 µm, approximately 40 µm, approximately 50 µm, approximately 60 µm, approximately 70 µm, approximately 80 µm, approximately 90 µm, approximately 100 µm). Width, as used herein, may refer to the extent of at least a portion of an EAP element in a dimension transverse to that of the expected electrostatic field.

EAP element 206 may include any suitable polymer material capable of deforming in the presence of an induced E-field. In some embodiments, EAP element 206 may include a dielectric polymer material. Additionally, or alternatively, EAP element 206 may include an elastomeric polymer material. Examples of polymer materials forming EAP element 206 may include, without limitation, acrylates, styrenes, polyesters, polycarbonates, epoxies, halogenated polymers, such as polyvinylidene fluoride (PVDF), copolymers of PVDF, such as poly(vinylidenefluoride-co-trifluoroethylene) (P[VDF-TrFE]), silicone polymers, such as polydimethylsiloxane (PDMS), and/or any other suitable polymer materials. Dielectric constants of such materials utilized in EAP elements may be a dielectric material with a suitable dielectric constant or relative permittivity, such as, for example, a dielectric constant ranging from approximately 2 to approximately 30.

In at least one embodiment, a dielectric material (i.e., an insulating material) may be disposed between EAP element 206 and at least one of primary electrode 202 or secondary electrode 204. For example, a dielectric coating or layer may be applied to primary electrode 202 and/or secondary electrode 204 such that the dielectric coating is disposed between the corresponding electrode and its associated surface of EAP element 206. Dielectric constants of such dielectric coatings may range, for example, from approximately 2 to approximately 30.

Figure 3:
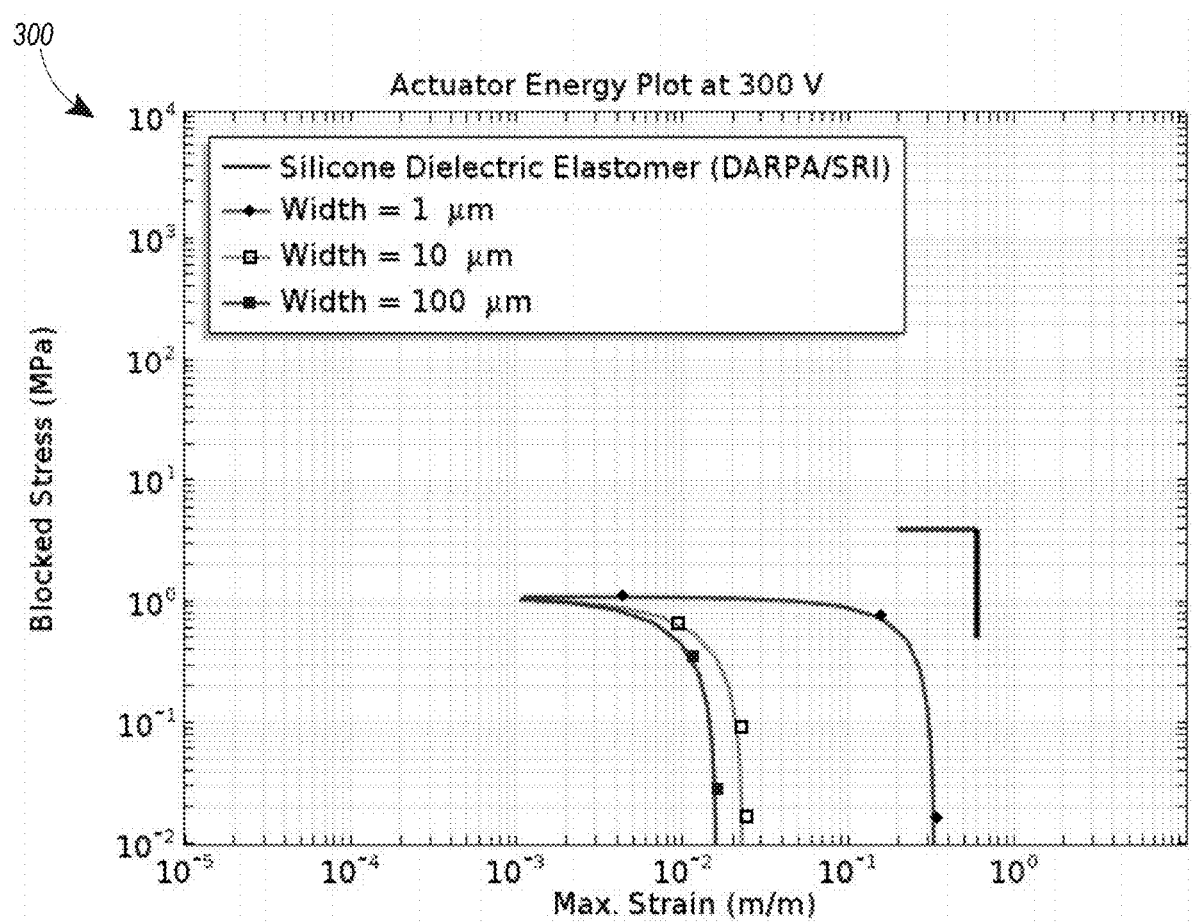
FIG. 3 is a graph showing the impact of changing aspect ratio of an exemplary actuator (width to thickness) with other factors being held constant in accordance with some embodiments.

FIG. 3 shows the impact of changing an aspect ratio of an electroactive device with other factors being held constant. In this case, the electroactive devices shown in FIG. 3 are electroactive actuators that each include an EAP element between a pair of electrodes (see, e.g., FIGS. 1-2C). A thickness of an EAP element of each of the electroactive devices is 1 µm and a potential difference of 300 volts has been applied between paired electrodes of each of the electroactive devices. FIG. 3 demonstrates that, for a given blocked stress level, smaller EAP widths yield greater strains and/or greater capacity for energy storage.

In some embodiments, an EAP element may have surfaces that are in total or substantial areal contact with a corresponding electrode. As previously noted, an EAP element in the presence of an electrostatic field may contract along the lines of that field, while expanding along the lateral dimensions in order to preserve volume and resulting in non-uniformities in deformation (e.g., non-uniformities in EAP portions extending beyond lateral edges of abutting electrodes). In some embodiments, EAP elements may have 2-dimensional extruded shapes and/or 3-dimensional shapes (e.g., a 3D patterned shape) (see, e.g., FIGS. 4A-6C and 14-16 showing views of 2D and/or a 3D arrangements).

In various embodiments, an electroactive device may include a plurality of EAP elements separated by gaps or inter-EAP element regions (i.e., interstices), in which a different material and/or volume than that of the EAP element may be present. These gaps may be located between adjacent EAP elements of the plurality of EAP elements and may, for example, be coplanar with the EAP elements. As in other embodiments presented herein, each of the plurality of EAP elements may include a first surface and a second surface opposite that first surface. Such a device may also include two sets of electrodes, with each member of each set of electrodes being placed in close proximity to or physically adhered to a corresponding surface of one or more EAP elements. In some embodiments the plurality of EAP elements may be arranged in a coplanar or substantially coplanar fashion.

These afore-described interstices or gaps may be volumes into which each of the EAP elements of an electroactive device may expand transversely upon compression by the force of an electrostatic field. Thus, upon E-field induced deformation, an EAP element may at least partially occlude or infill adjacent gaps or interstitial volumes. The ratio of an interstitial volume to the volume of an adjacent EAP element may be adjusted so as to create a desired level of uniformity in the deformations when the EAP element is subjected to an electrostatic field of at least a given field strength. In some embodiments, the interstitial volume may be adjusted according to the Poisson's ratio of the EAP material.

Each of the gaps/interstitial volumes may include any suitable material, without limitation. In some examples, the gaps may include a fluid, such as a gaseous composition (e.g., air, etc.) that is readily compressed and/or displaced. In at least one example, the volumes may include a material with or without a dipole moment, or a combination of both.

The gap material may be inert or have reactivity to compression. The gap material may be doped with certain other materials that may alter its response characteristics to an electrostatic field. The gap material and any dopants therein may be transparent to visible light. According to some embodiments, EAP elements may each have a shape that facilitates expansion into adjacent interstitial regions and/or that yields a more uniform strain distribution when the EAP material is subjected to an electrostatic field of a given field strength.

In some embodiments, a cross-sectional profile of an EAP element may be quadrilateral. In some embodiments, an EAP element shape may be that of a 3D quadrilateral and/or parallelepiped (e.g., a parallelogram). At least one angle may be defined to specify the 2D or 3D shape or form of the EAP element and/or at least a portion thereof. This at least one angle may be the interior angle that a third surface, such as one that extends from the first EAP element surface to the second EAP element surface, makes with respect to the direction of the expected electrostatic field. Additional angles may be defined to specify more complicated quadrilateral/parallelepiped or other geometric forms. The inside or interior angle that is formed between the electrostatic field direction and this third surface or other defined surfaces may be non-zero. In some embodiments, the interior angle may range from approximately 0° to approximately 70°. This angle may also be referred to as the cant angle.

FIGS. 4A-C are depictions of an exemplary electroactive device 400 undergoing various levels of compression: 0%, 36%, and 72%, respectively. Within this electroactive device, a plurality of 1 µm wide EAP elements 402 (the dark regions) are laterally surrounded by 1 µm air-filled gaps or interstitial volumes 404 (the light spaces). The shading level indicates the von Mises's stresses in MPa for EAP elements 402 depicted in each of FIGS. 4A-C. Compression here refers to a difference between the undeformed thickness and the deformed thickness relative to the undeformed (or maximum) thickness. In these figures, the direction of the electrostatic field is parallel to the Y-axis, while the transverse dimension is represented by the X-axis.

FIG. 4A shows a cross-sectional view of electroactive device 400 in an uncompressed state (i.e., 0% compression). Electroactive device 400 includes an array of EAP elements 402 that are spaced from each other by interstitial volumes 404. These EAP elements 402 each include a first (depicted as the top) surface 406 and a second (depicted as the bottom) surface 408. Each EAP element also includes side surfaces, including third surface 410 and fourth surface 412, each of which extends from first surface 406 to second surface 408. In this depiction, the interior or cant angle is 0°. As will be described in greater detail below with reference to FIGS. 15 and 16, one or more electrodes and/or material layers may abut first and second surfaces 406 and 408 and/or adjacent portions of interstitial volumes 404.

In FIG. 4B, a cross-sectional view of electroactive device 400 with a plurality of EAP elements 402 that have been compressed by 36%. This figure demonstrates the expansion of EAP elements 402 into the adjacent interstitial volumes 404.

In FIG. 4C, a cross-sectional view of electroactive device 400 is shown after EAP elements 402 have been compressed by 72%. In this view, the transverse expansion (along the indicated X-axis) of EAP elements 402 has substantially infilled the adjacent interstitial volumes 404, providing a more substantially uniform strain within EAP elements 402 of electroactive device 400.

Figure 5A:
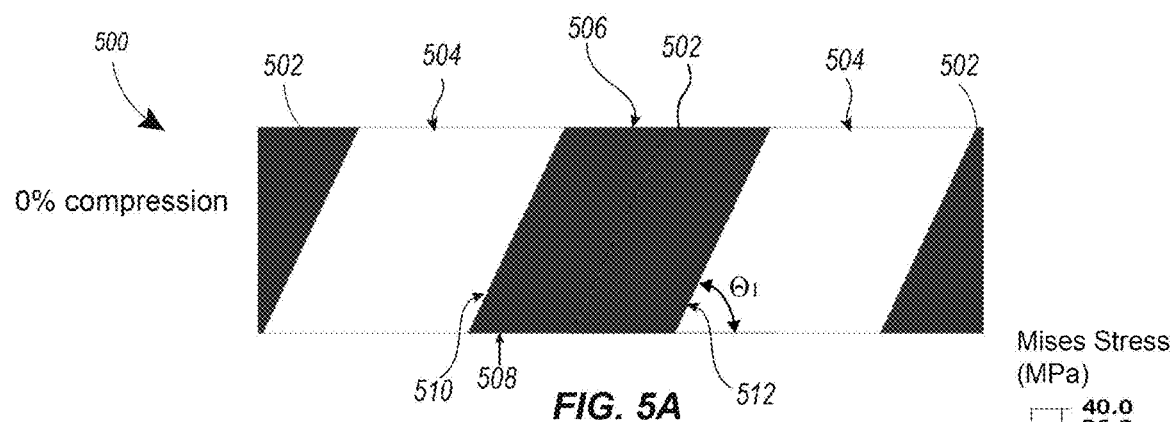
FIGS. 5A-5C are cross-sectional views of an exemplary electroactive device structure that includes an array of EAP elements in accordance with some embodiments.
Figure 5B:
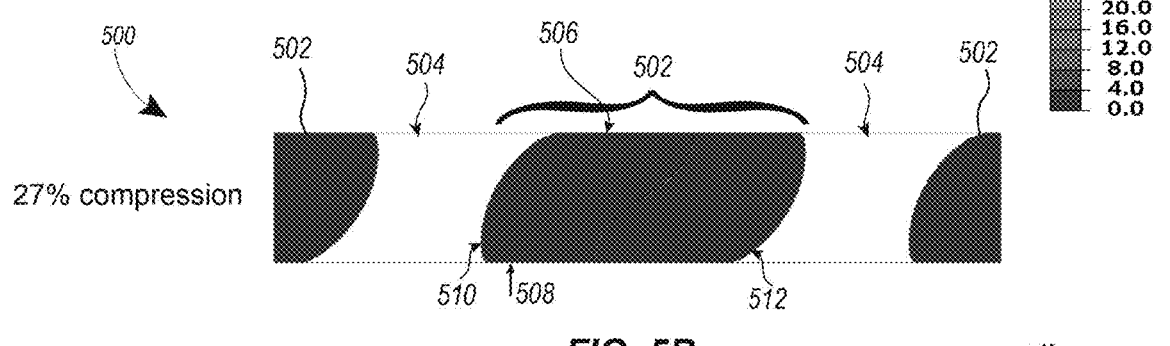
Figure 5C:
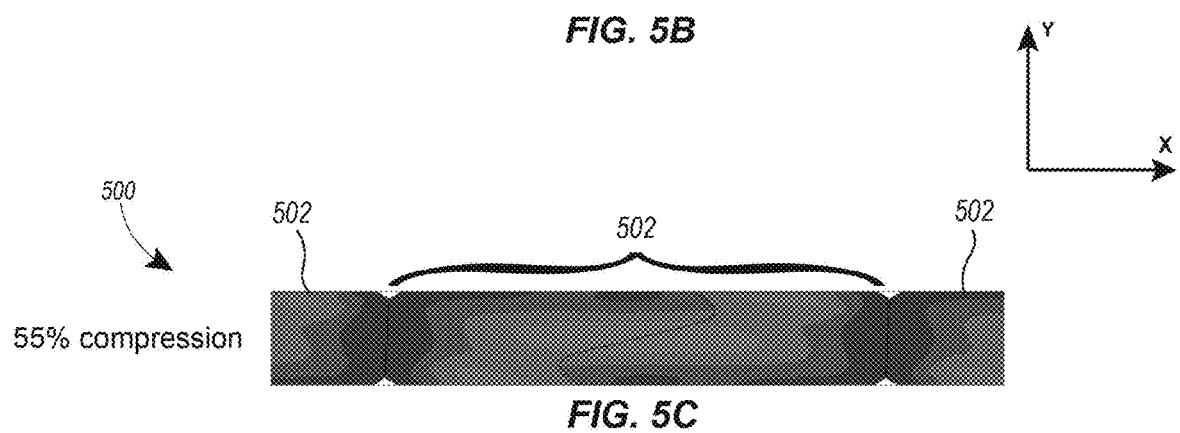

FIGS. 5A-C are depictions of an exemplary electroactive device 500 including a plurality of EAP elements 502 undergoing different levels of compression. In the undeformed state depicted in FIG. 5A, EAP elements 502 are canted at an interior angle of 25°, which is the complement of the indicated angle $\Theta_1=65°$. The three different views, FIG. 5A, FIG. 5B, and FIG. 5C each corresponds to a different level of compression, which are, respectively, 0%, 27%, and 55%. EAP elements 502 in FIGS. 5A-C are 1 µm wide elastomeric polymer elements (the dark regions) and are adjacent to 1 µm wide gaps (the light spaces). The shading level indicates the von Mises's stresses in MPa. In these figures, the direction of the electrostatic field is parallel to the Y-axis, while the transverse dimension is represented by the X-axis.

FIG. 5A shows a cross-sectional view of electroactive device 500 including an array of 25° canted EAP elements 502 which are spaced from each other by air-filled interstitial volumes 504. These EAP elements 502 each include a first (depicted at the top) surface 506 and a second (depicted at the bottom) surface 508. Each EAP element includes two opposing side surfaces including third surface 510 and fourth surface 512, each of which extends from first surface 506 to second surface 508. EAP elements 502 depicted in FIG. 5A are uncompressed.

In FIG. 5B, EAP elements 502 of electroactive device 500 have been compressed by 27%, revealing how EAP elements 502 expand approximately transversely to infill partially their adjacent interstitial volumes 504.

In FIG. 5C, EAP elements 502 of electroactive device 500 have been further compressed in this depiction to a compression of 55%. This level of compression is less than the 72% compression for the exemplary electroactive device 400 of FIG. 4C, which does not possess canted EAP elements. A greater uniformity in von Mises's stress levels is evident due to the 25° canting of the EAP elements 502. A comparative inspection of the results of FIGS. 4A-C and those of FIGS. 5A-C substantiates that the level of uniformity achievable may increase with a non-zero cant angle. Moreover, the von Mises's stress levels may be reduced with a non-zero cant angle, as illustrated in FIGS. 5A-C.

Figures 6A, 6B, 6C:
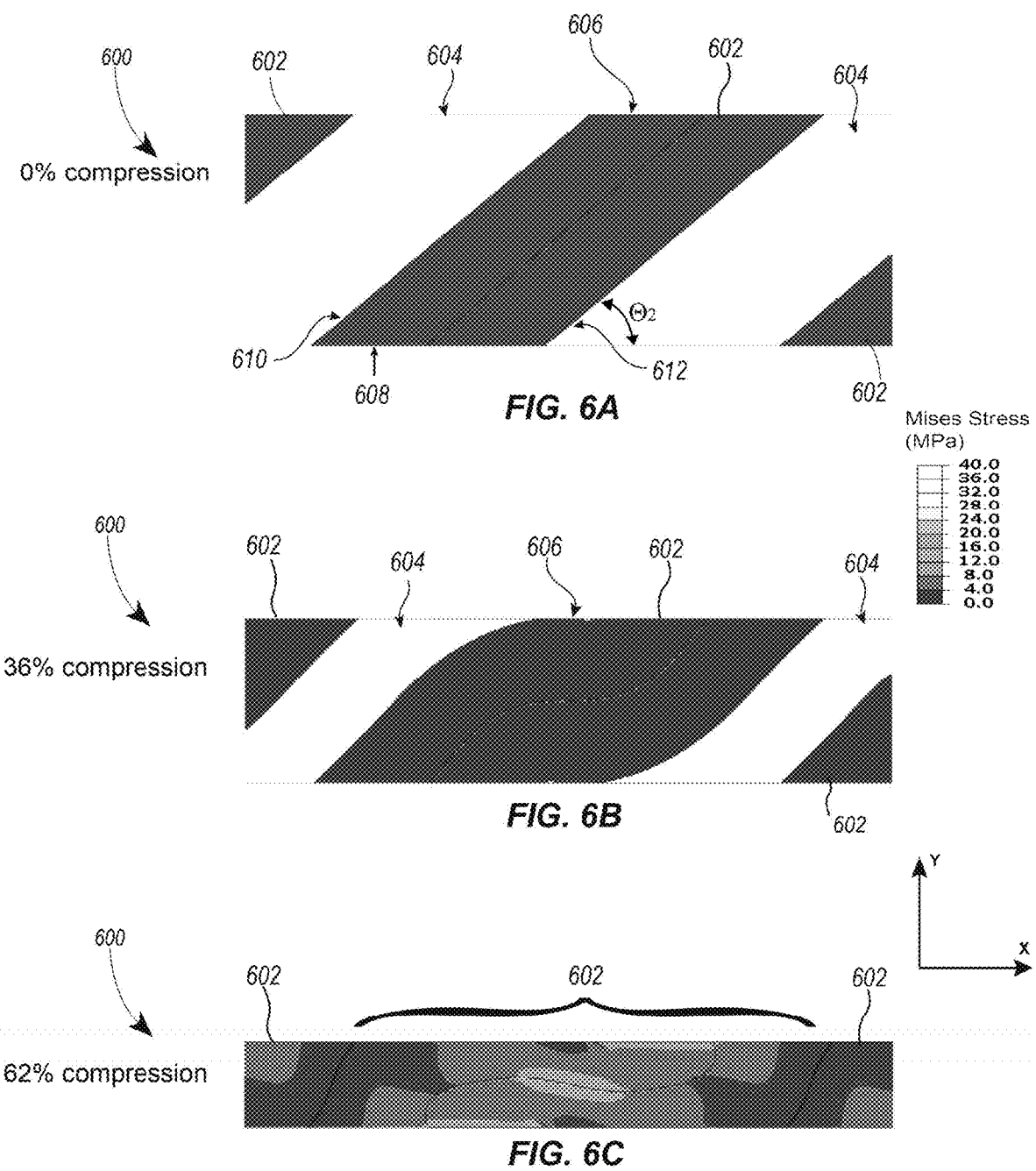
FIGS. 6A-6C are cross-sectional views of an exemplary electroactive device structure that includes an array of EAP elements in accordance with some embodiments.

In FIGS. 6A-C, an exemplary electroactive device 600 is depicted undergoing various levels of compression, similar to the depictions presented in FIGS. 4A-C and in FIGS. 5A-C. EAP elements 602 are also 1 µm wide elastomeric polymer elements that are laterally surrounded by 1 µm air-filled interstitial volumes 604. Each of EAP elements 602 in this depiction includes a first surface 606, a second surface 608, and two opposing side surfaces including third surface 610 and fourth surface 612. The cant angle of each of EAP elements 602 in the undeformed state is 50°, which is the complement of the indicated angle $\Theta_2=40°$. In FIGS. 6A-C, the direction of the electrostatic field is parallel to the Y-axis, while the transverse dimension is visually represented by the X-axis.

In FIG. 6A, EAP elements 602 are in an uncompressed state. In FIG. 6B, EAP elements 602 of electroactive device 600 have been compressed by 36% resulting in the expansion of EAP elements 602 at least partially infilling the adjacent interstitial volumes 604.

In FIG. 6C, EAP elements 602 of electroactive device 600 have been further compressed by 62%, resulting in additional infilling of the interstitial volumes 604. The infilling of interstitial volumes 604 with this compression of 62% approaches a unity filling factor (fractional contribution of the EAP material to the interstitial volume). The resultant uniformity in stress is evident from the narrow and low range of von Mises's stress indicated by the gray levels.

The net result of the relative inspections of FIGS. 6A, 6B, and 6C suggests that canting of EAP elements 602 obliquely may permit a greater uniformity in strain of the electroactive device upon compression, and thus may yield concomitantly lower stress in EAP elements 602.

Figure 7:
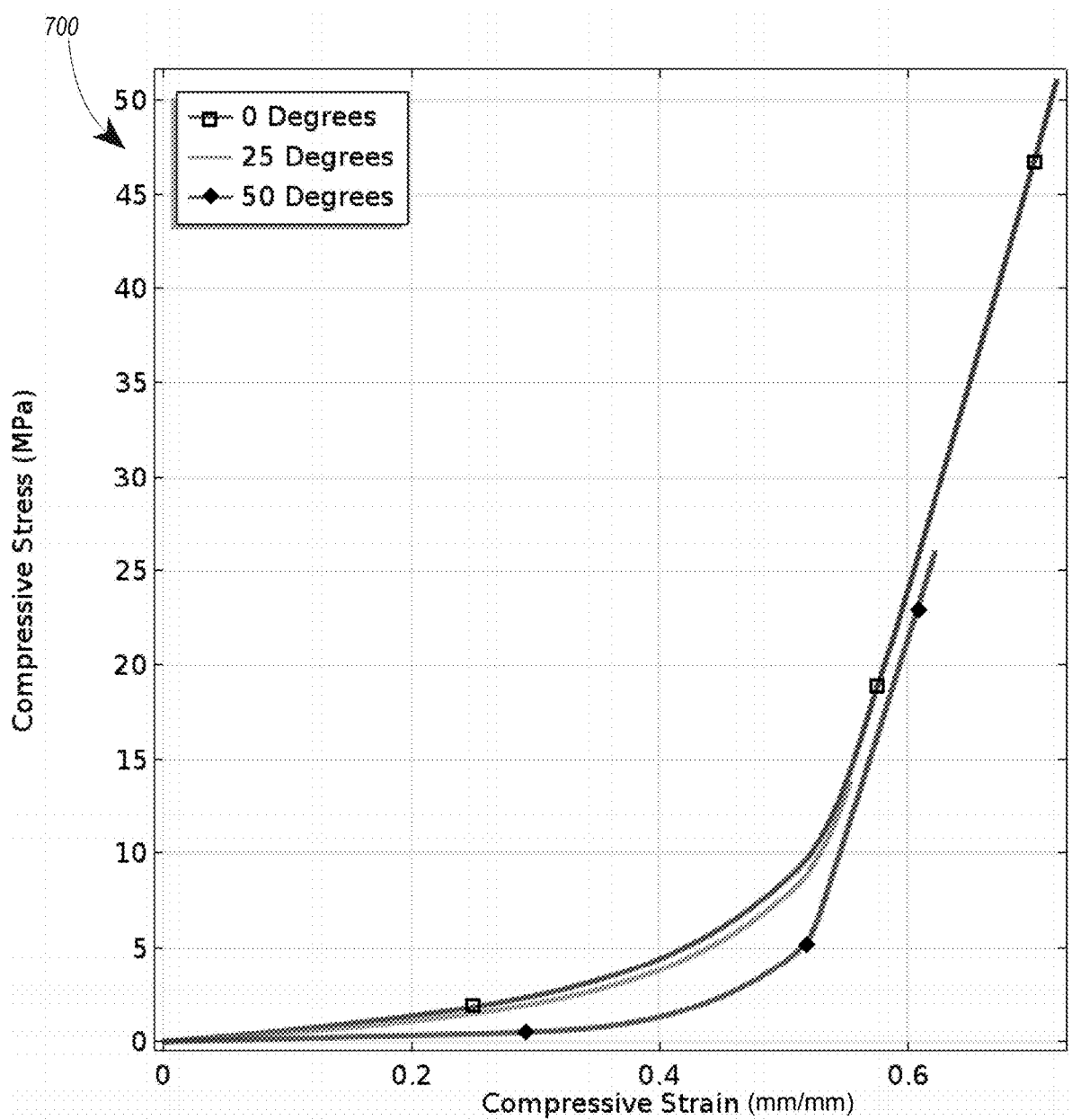
FIG. 7 is a graph showing compressive stress as a function of compressive strain for three electroactive devices in accordance with some embodiments.

FIG. 7 shows the relationship between compressive strain (in units of mm/mm) and compressive stress (in MPa) for electroactive devices having three different values of EAP element cant angle: 0°, 25°, and 50°. This shows that the increased cant angle may aid in increasing strain while lowering the associated stress. As shown in this figure, the uniformity of strain also increases with the angle.

Figure 8:
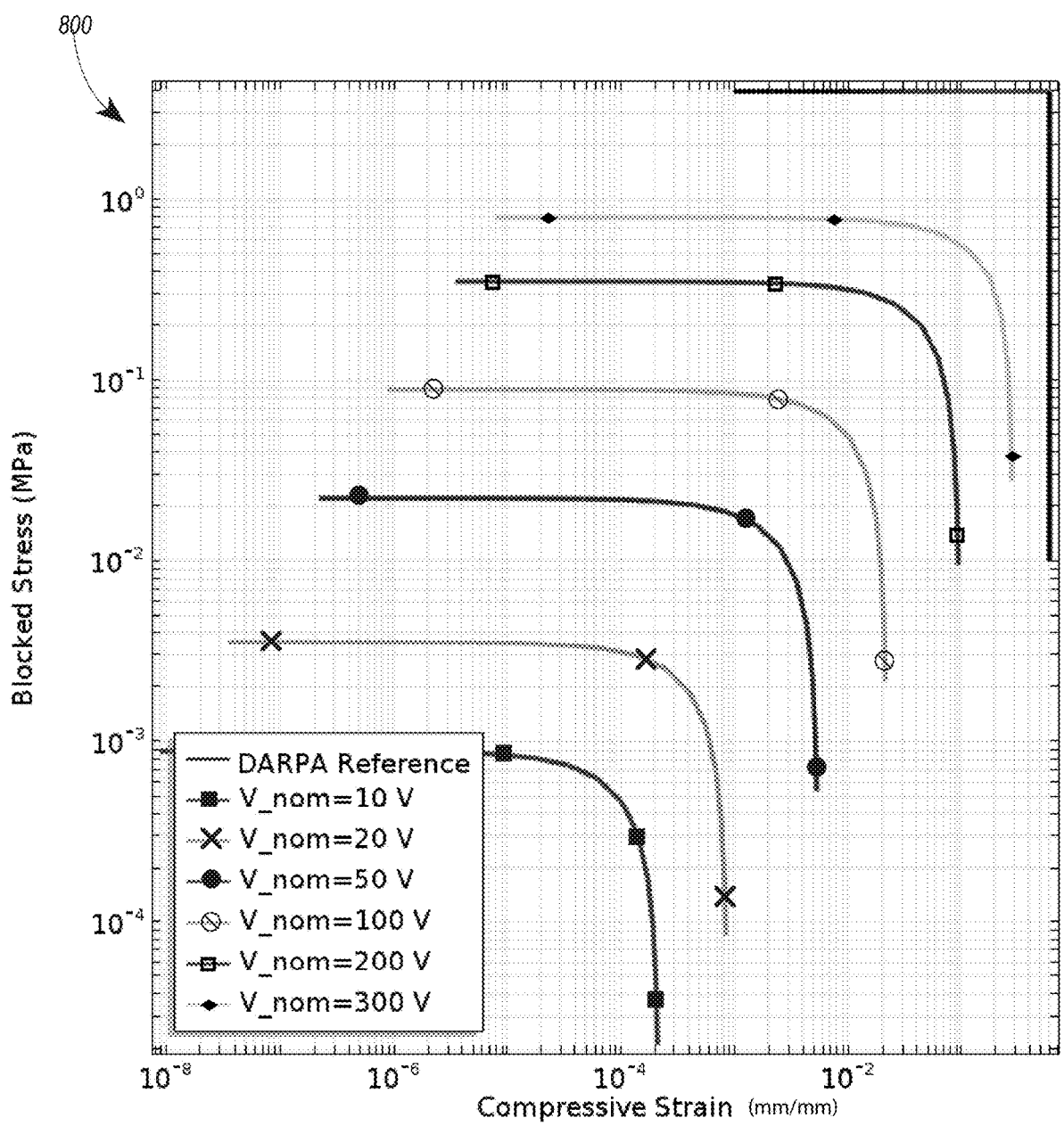
FIG. 8 is a graph showing blocked stress vs compressive strain for a range of voltages for an EAP device in accordance with some embodiments.
Figure 9:
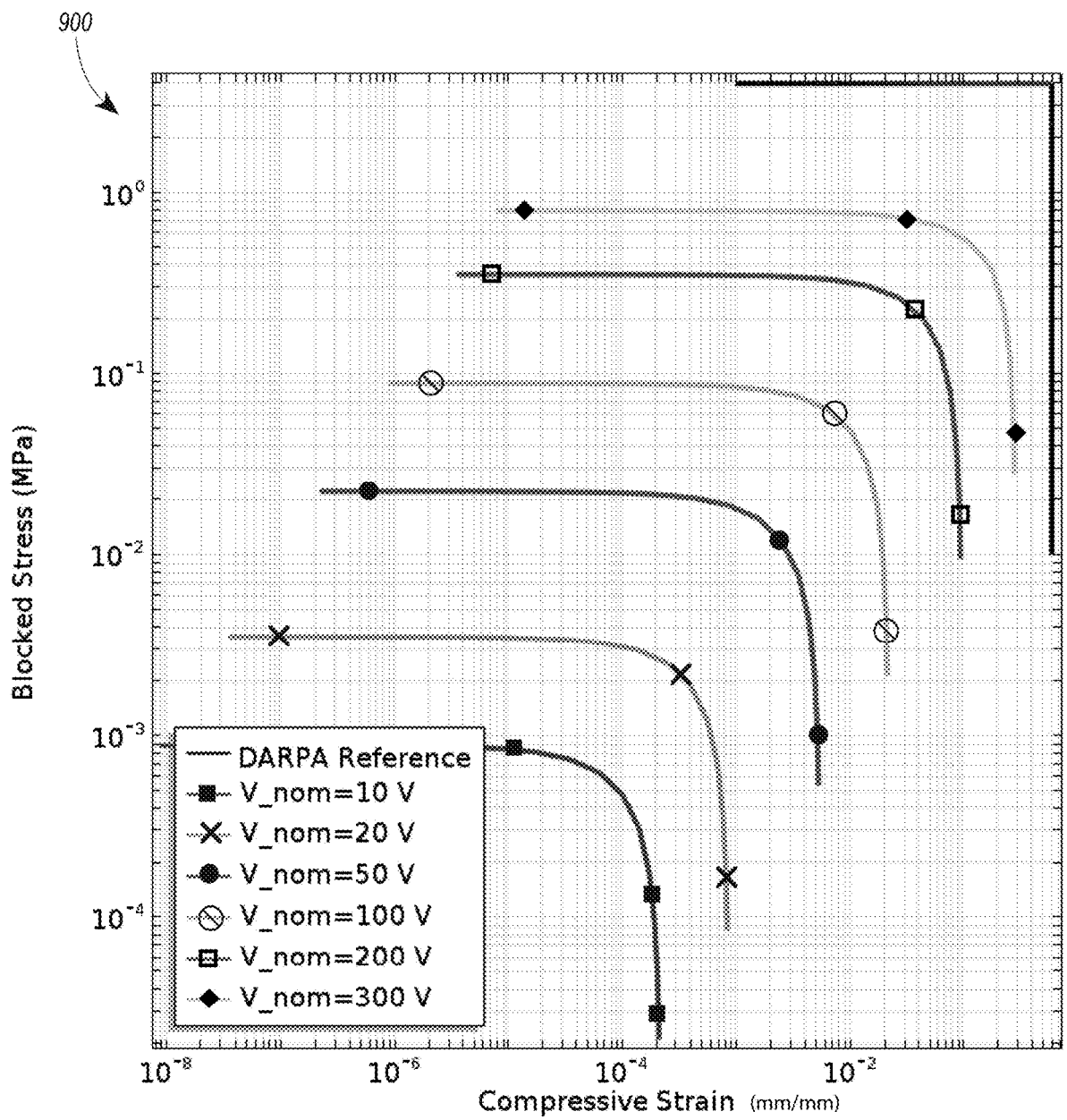
FIG. 9 is a graph showing blocked stress vs compressive strain for a range of voltages for an EAP device in accordance with some embodiments.
Figure 10:
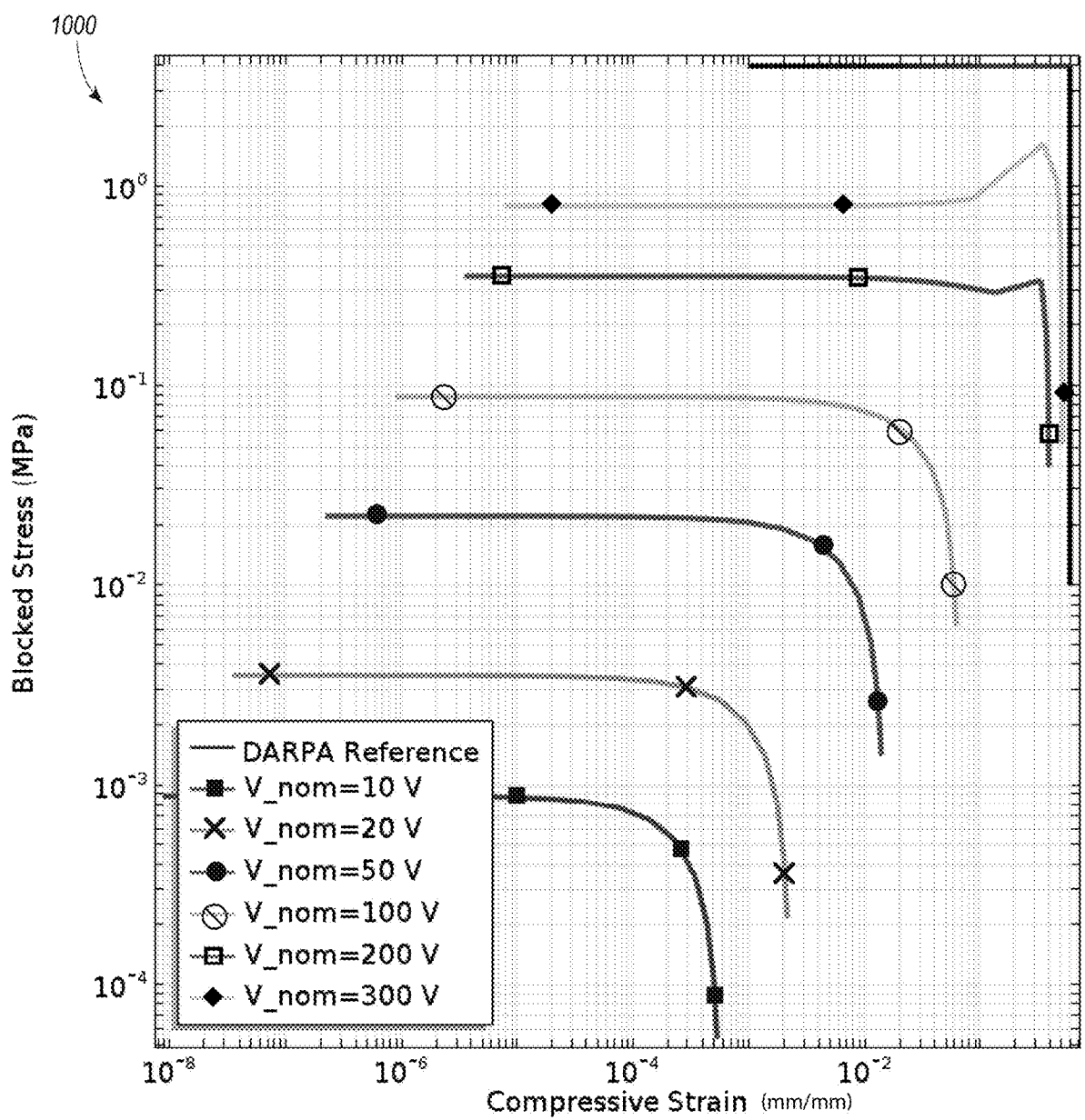
FIG. 10 is a graph showing blocked stress vs compressive strain for a range of voltages of an EAP device in accordance with some embodiments.

FIGS. 8, 9, and 10 demonstrate how blocked stress (MPa) may vary with compressive strain (mm/mm) as a function of voltage at six different values of voltage: 10V, 20V, 50V, 100V, 200V, and 300V. The cant angles of EAP elements of electroactive devices in FIGS. 8, 9, and 10 are respectively 0°, 25°, and 50°. Blocked stress in these examples refers to stress produced by the EAP material when one of the strain principal components is constrained to be zero (free strain and blocked stress are two of the common ways to characterize the performance of a material). The results shown in FIGS. 8, 9, and 10 demonstrate that higher voltages applied to EAP elements, as well as increased cant angles of the EAP elements, may increase the compressive strain and forces on abutting electrodes.

Figure 11:
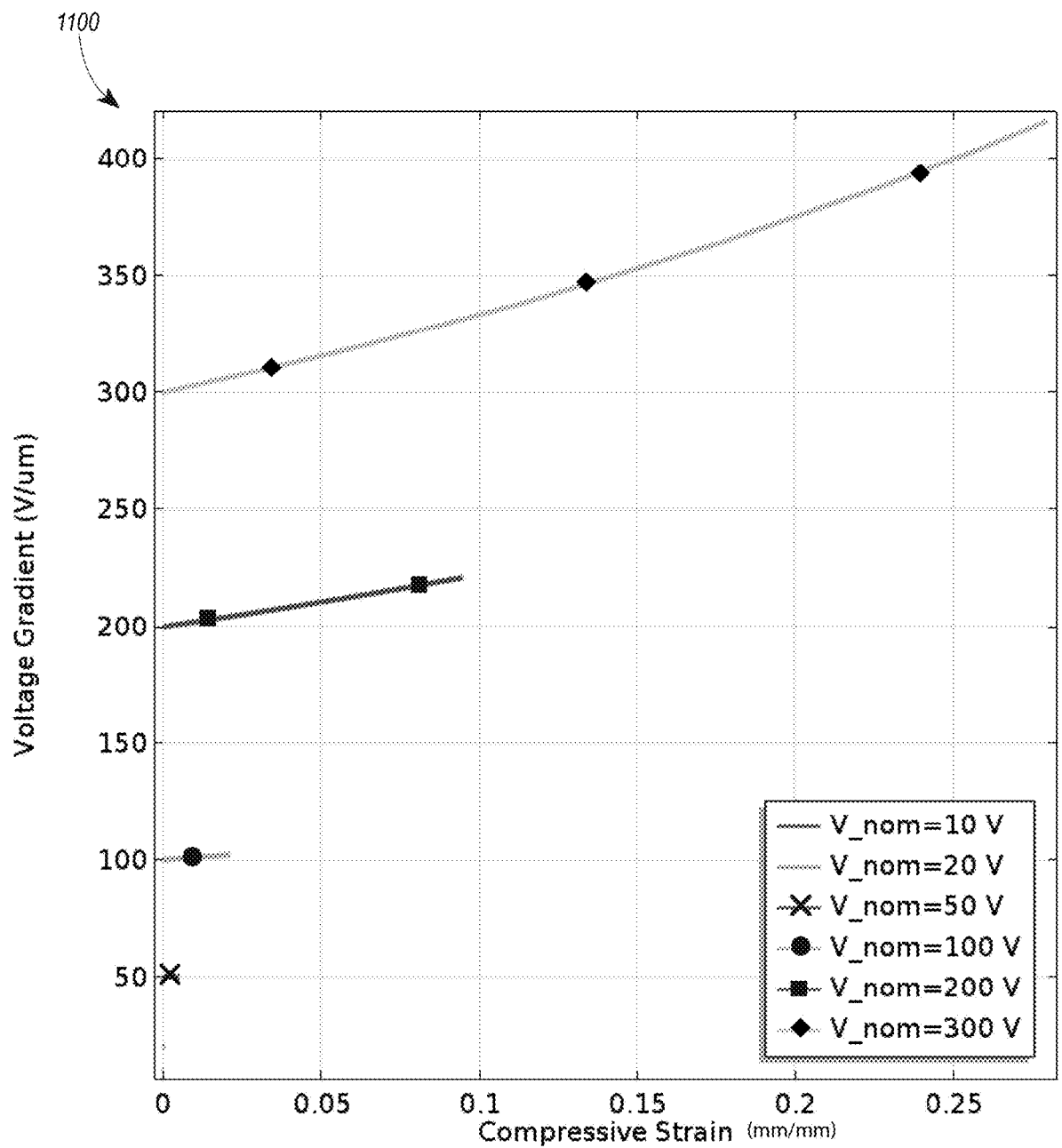
FIG. 11 is a graph showing voltage gradient vs compressive strain as a function of voltage for an exemplary electroactive device in accordance with some embodiments.
Figure 12:
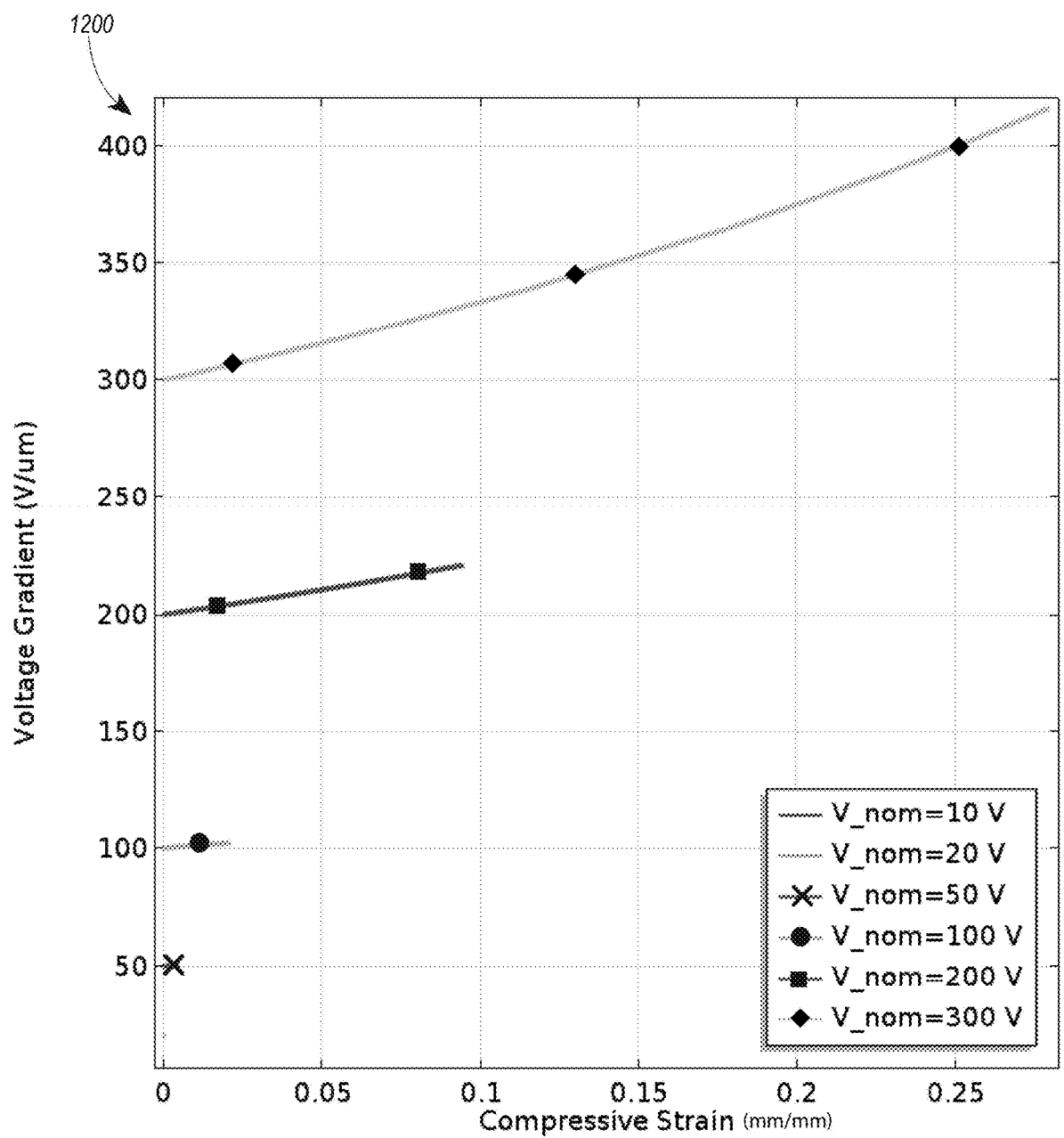
FIG. 12 is a graph showing voltage gradient vs compressive strain for a range of voltages for an exemplary electroactive device in accordance with some embodiments.
Figure 13:
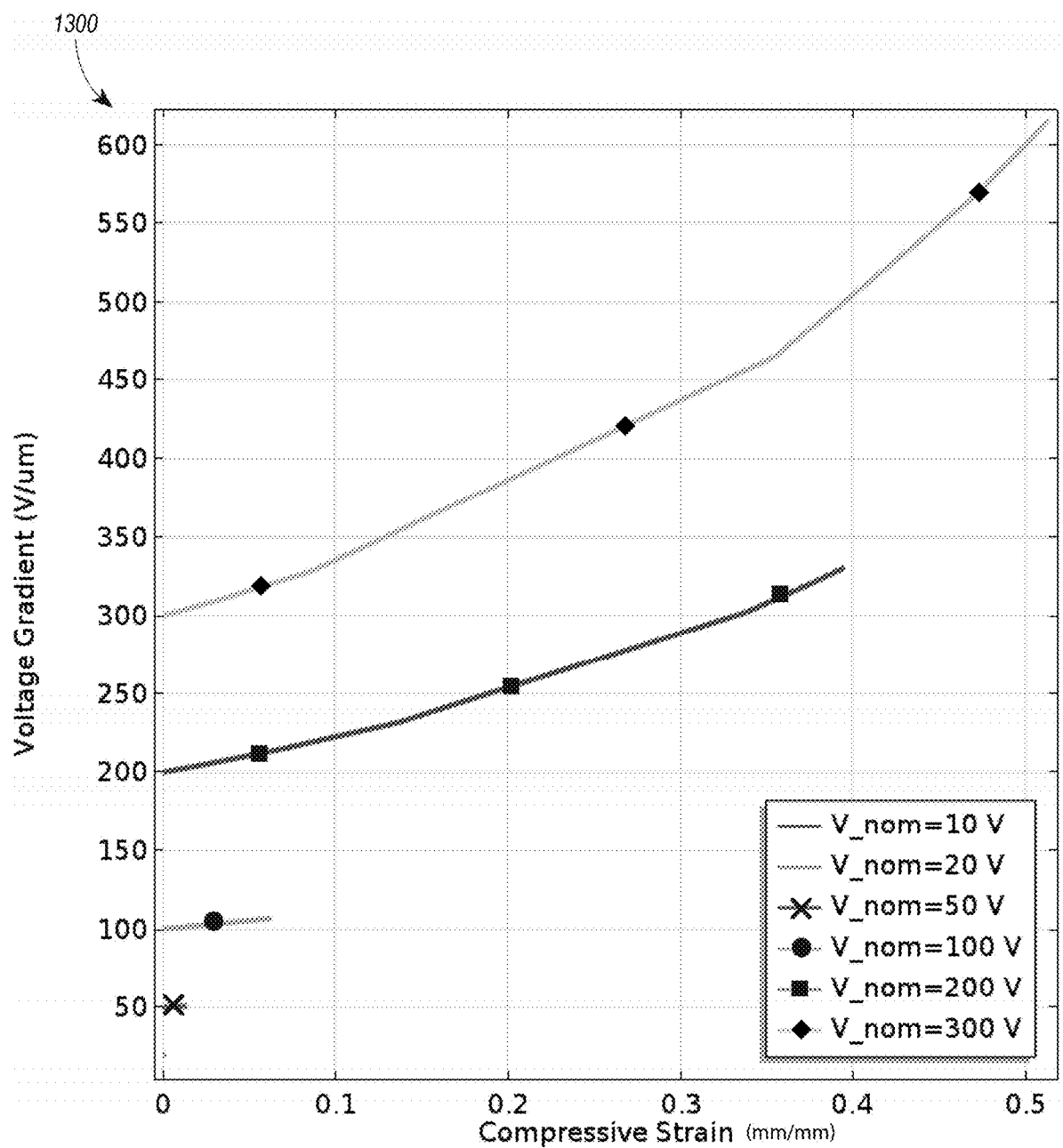
FIG. 13 is a graph showing voltage gradient vs compressive strain for an exemplary electroactive device in accordance with some embodiments.

FIGS. 11, 12, and 13 each show voltage gradient (i.e., magnitude of the electrostatic field) for EAP elements of electroactive devices as a function of compressive strain (mm/mm) at six different values of voltage: 10V, 20V, 50V, 100V, 200V, and 300V. The values of voltage gradient are in volts per micron. The cant angles of EAP elements in FIGS. 11, 12, and 13 are respectively 0°, 25°, and 50°. Inspection of these figures suggests that the compressive strain (mm/mm) nearly doubles for an E-field strength of 350 V/micron in the 50° canted EAP material, while in the less canted EAP material of 25°, the strain is less than half that value at a much lower E-field strength of 100 V/micron. The results shown in FIGS. 11, 12, and 13 demonstrate that higher voltages applied to EAP elements, as well as increased cant angles of the EAP elements, may increase the compressive strain and forces on abutting electrodes.

In additional or alternative embodiments, each of a set of EAP elements may extend in a longitudinal or an elongation direction approximately transverse to the electrostatic field. In some of these embodiments, the elongation direction of each elongated EAP element may be approximately parallel to a common direction, or alternatively, may vary in direction with respect to one another.

Figure 14A:
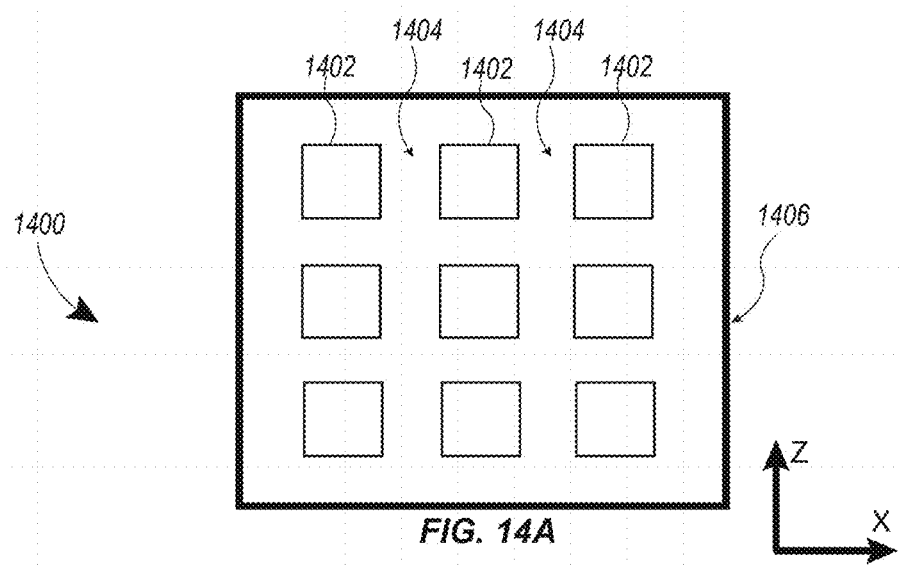
FIGS. 14A-C depicts three exemplary electroactive device structures that include arrays of EAP elements as viewed perpendicular to a plane of the array of elements in accordance with some embodiments.
Figure 14B:
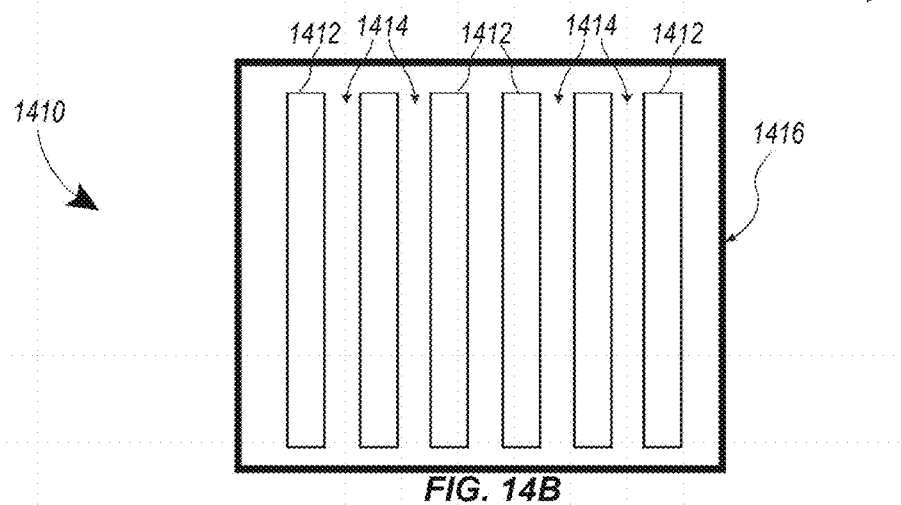
Figure 14C:
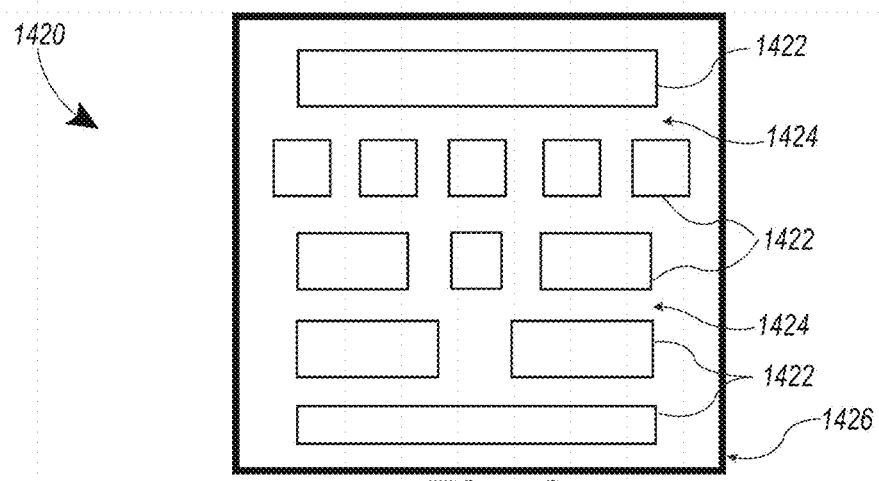

FIGS. 14A-C present schematic top views of three separate electroactive devices, 1400, 1410, and 1420 respectively, each with a different configuration and arrangement of a plurality of separate arrayed EAP elements 1402, 1412, and 1422, in FIGS. 14A to 14C, respectively, and each in accordance with some embodiments. The respective gaps 1404, 1414, and 1424 (i.e., interstitial volumes) in FIGS. 14A-C between EAP elements 1402, 1412, and 1422 may be a gas (e.g., air), a dielectric material, an inert material, or a non-electroactive material. The viewpoint, in each of these figures, is one that is essentially parallel to the electrostatic field lines, perpendicular to the indicated XZ plane (along the Y-direction given in FIGS. 1, 2 and 4-6)

FIG. 14A is a schematic of an exemplary electroactive device 1400 with a 3×3 array of similar EAP elements 1402. This electroactive device includes an outer surface 1406. Surrounding each of EAP elements 1402 are gaps or interstitial volumes 1404.

In FIG. 14B, an exemplary electroactive device 1410 is depicted having a 1×6 array of elongated (along the Z-direction) EAP elements 1412, spaced from each other by interstitial volumes 1414. The electroactive device 1410 includes an outer surface 1416.

In FIG. 14C, an exemplary embodiment of an electroactive device 1420 is depicted including a plurality of EAP elements 1422, each surrounded by one or more interstitial volumes 1424. This particular depiction, in accordance with some embodiments, indicates that the EAP elements 1422 of an actuator or device may vary in characteristics, including size, shape, spacing, and/or layout.

Figure 15:
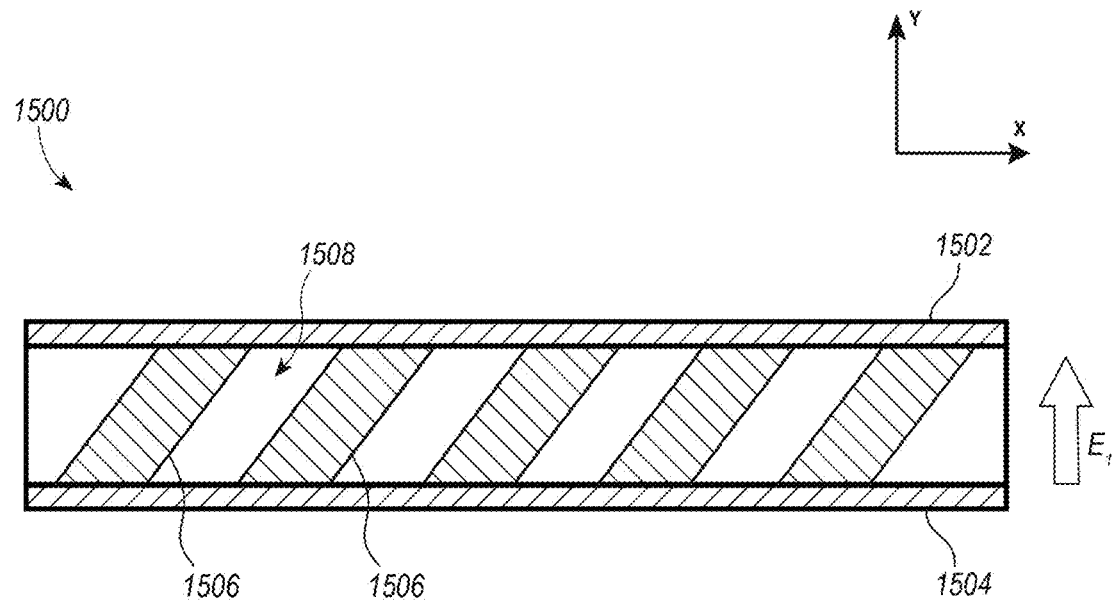
FIG. 15 shows a cross-sectional view of an exemplary electroactive device structure that includes an array of EAP elements in accordance with some embodiments.

FIG. 15, shows a cross-sectional view of an electroactive device 1500 including two electrodes 1502 and 1504, and disposed therebetween are a plurality of EAP elements 1506 each with adjacent gaps or interstitial volumes 1508. These EAP elements are canted at an angle of approximately 45°. The direction $E_1$ of the lines of the electrostatic field between electrode 1502 and electrode 1504 is shown in this figure. The sizes of the various components in FIG. 15 are not necessarily to relative scale.

Figure 16:
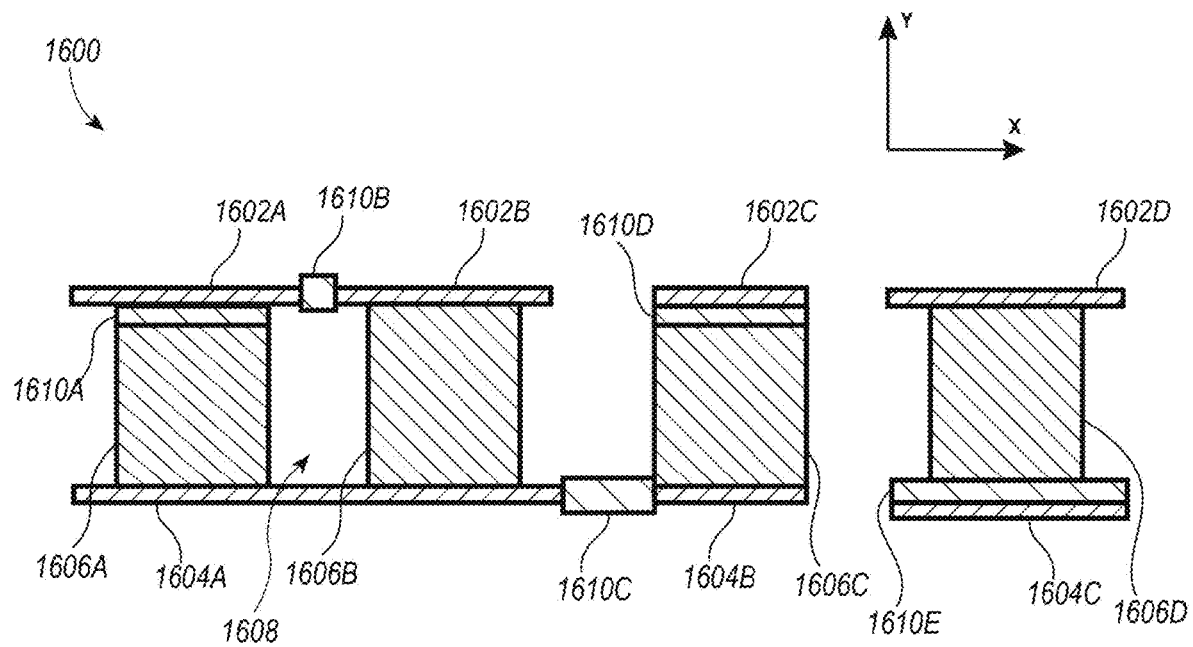
FIG. 16 shows cross-sectional views of exemplary arrangements of EAP elements in electroactive device structures in accordance with some embodiments.

FIG. 16, shows a cross-sectional view of an electroactive device 1600 including a plurality of EAP elements 1606A, 1606B, 1606C, and 1606D. Each of these EAP elements is disposed, respectively, between electrodes 1602A and 1604A, 1602B and 1604A, 1602C and 1604B, and 1602D and 1604C. The various components in FIG. 16 are not necessarily to relative scale.

In accordance with some embodiments, EAP element 1606A, which is disposed between electrodes 1602A and 1604A, may include additionally, a dielectric material 1610A disposed between electrode 1602A and EAP element 1606A. Dielectric material 1610A may possess, for example, a dielectric constant from approximately 2 to approximately 30.

Dielectric material also may be disposed between electrodes. For example, as shown in FIG. 16, an insulator, such as dielectric material 1610B, may be disposed between electrodes 1602A and 1602B. These electrodes are associated with adjacent EAP elements 1606A and 1606B, respectively. This dielectric material may possess the same dielectric constant and/or a different dielectric constant than other dielectric materials 1610A, 1610C, 1610D, and 1610E illustrated in this figure.

A similar arrangement is depicted in FIG. 16 between electrodes 1604A and 1604B. A dielectric material 1610C may be interposed between electrodes 1604A and 1604B. Dielectric material 1610C may possess the same dielectric constant and/or a different dielectric constant than other dielectric materials 1610A, 16106, 1610D, and 1610E.

The presence of a dielectric material in an actuator or device is further indicated in FIG. 16. EAP element 1606C has paired electrodes 1602C and 1604B and a dielectric material 1610D is disposed between electrode 1602C and the EAP element 1606C. In some examples, EAP element 1606D may be separated from one of its electrodes 1604C with a dielectric material 1610E.

In FIG. 16, EAP elements 1606A and 1606B are separated by a gap or interstitial volume 1608. As shown in this figure, EAP elements 1606A and 1606B share a common secondary electrode 1604A, but do not directly share a common primary electrode. According to some embodiments, electrodes 1602A, 1602B, 1602C, 1602D, 1604A, 1604B, and/or 1604C shown in FIG. 16 may vary in composition and/or may possess different electrical properties. Additionally or alternatively, dielectric materials 1610A, 16106, 1610C, 1610D, and/or 1610E shown in this figure may vary in composition and/or may possess different electrical properties. In some examples, EAP elements 1606A, 1606B, 1606C, and/or 1606D may vary in composition and/or may possess different electromechanical responses to the same electrostatic field strength. In at least one example, paired electrodes 1602A/1604A, 1602B/1604A, 1602C/1604B, and/or 1602D/1604C may provide different electrostatic field strengths at various times. Additional or alternative electrode configurations may be utilized in electroactive devices in various embodiments.

Electroactive devices (e.g., electroactive actuators) as described herein may include at least two paired electrodes (e.g., opposing electrodes respectively specified as a primary electrode and a secondary electrode). When each of a primary electrode and a secondary electrode of paired electrodes are separately energized with a different potential, an electrostatic field may be produced. For a given electroactive device, either or both of the two electrodes may cover the entire first or second surface (i.e., common areal overlap) of the associated EAP elements (see, e.g., FIG. 15 showing electroactive device 1500 with electrodes 1502 and 1504 abutting first and second surfaces of EAP elements 1506). Alternatively, an electroactive device may include a pairing of a plurality of primary electrodes with a single common secondary electrode or vice versa (see, e.g., FIG. 16 showing electrodes 1602A and 1602B with common electrode 1604A). While the geometric depiction of EAP elements 1606A-D in FIG. 16 is of rectangular form, EAP elements may include quadrilateral or other geometric forms as shown and described herein.

According to some embodiments, a set of primary electrodes may have a first subset of electrodes with each member of that subset at a common first potential. A set of secondary electrodes may have a second subset of electrodes with each member of that subset at a common second potential. At least one electrode from the first subset may be paired with at least one electrode from the second subset.

In some embodiments, at least one of a primary electrode or a secondary electrode may be a movable such that the electrode is movable in conjunction with displacement of an abutting surface portion of the EAP element. According to at least one example, one of the primary or secondary electrodes may be a movable electrode and the other electrode may be a fixed electrode that holds an abutting or corresponding surface portion of the EAP element in a fixed position.

In some embodiments, at least one component may be added to the EAP material of an EAP element to alter its electromagnetic properties. For example, barium titanate ($BaTiO_3$), which is a member of the perovskite family and which may also include other titanates, and/or any other suitable component may be added to the EAP material. $BaTiO_3$ is a ferroelectric material with a relatively high dielectric constant (e.g., a value of between approximately 500 and approximately 7000) and polarization and may be used in various electroactive devices described herein. Besides large polarizability and permittivity, large strains may also achievable with $BaTiO_3$. Pure $BaTiO_3$ is an insulator whereas upon doping it may transform into a semiconductor.

Figure 17:
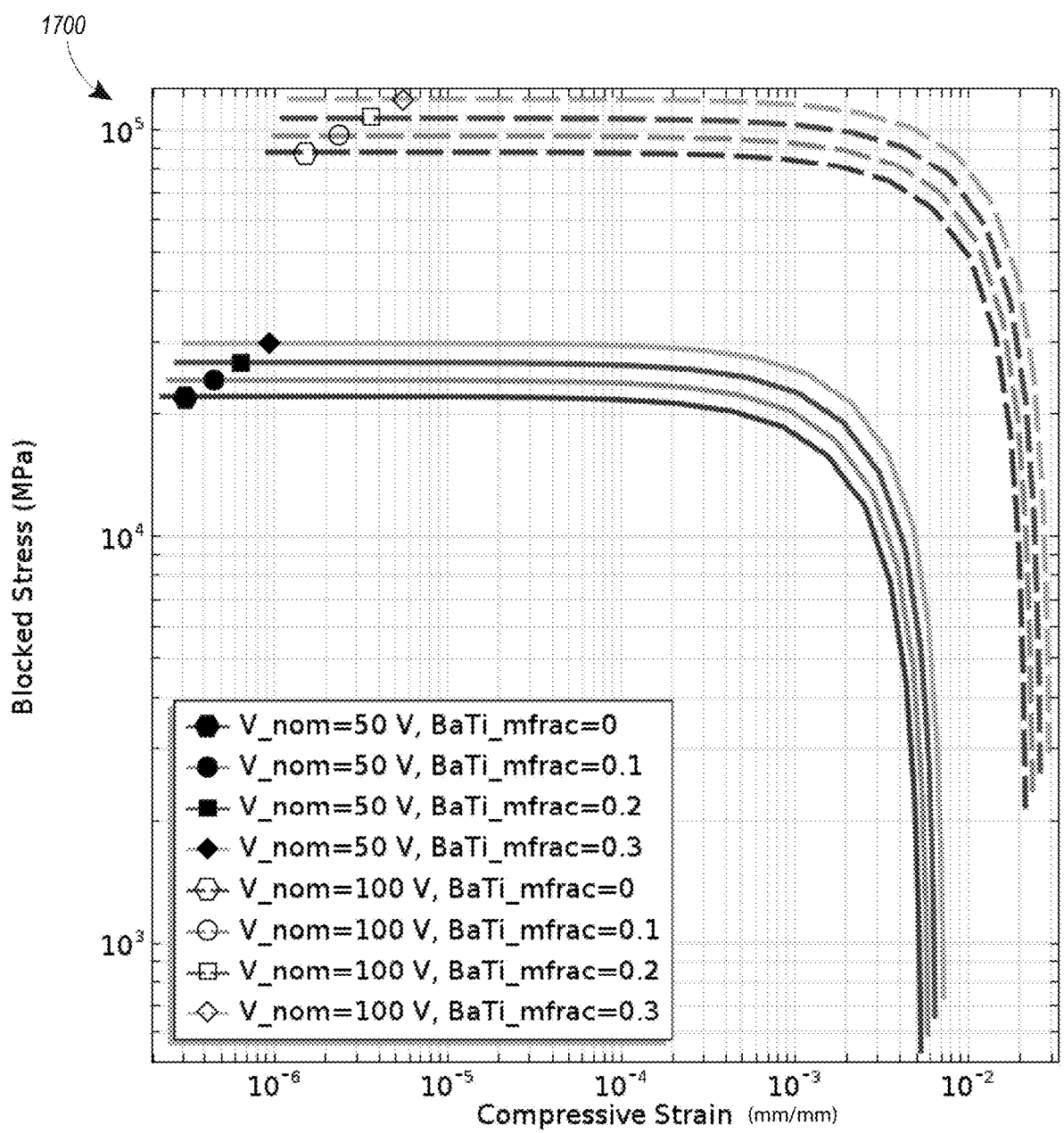
FIG. 17 is a graph showing the impact of incorporating barium titanate of various concentrations into an EAP element of an exemplary electroactive device structure in accordance with some of the embodiments.

FIG. 17 shows dependency of blocked stress (in MPa) on compressive strain (mm/mm) with various fractional contributions of the dopant $BaTiO_3$ to an EAP element of an electroactive device under two separate voltages. The increased content of $BaTiO_3$ in the EAP material may be indicative of an increased effective dielectric constant of the EAP element. As shown in this figure, for a given level of electrostatic field, a greater dielectric constant may provide a greater level of deformation or compression. The results shown in FIG. 17 demonstrate that the higher dielectric constants of the EAP materials (due to, for example, the addition of $BaTiO_3$) may increase the forces on abutting electrodes.

Figure 18:
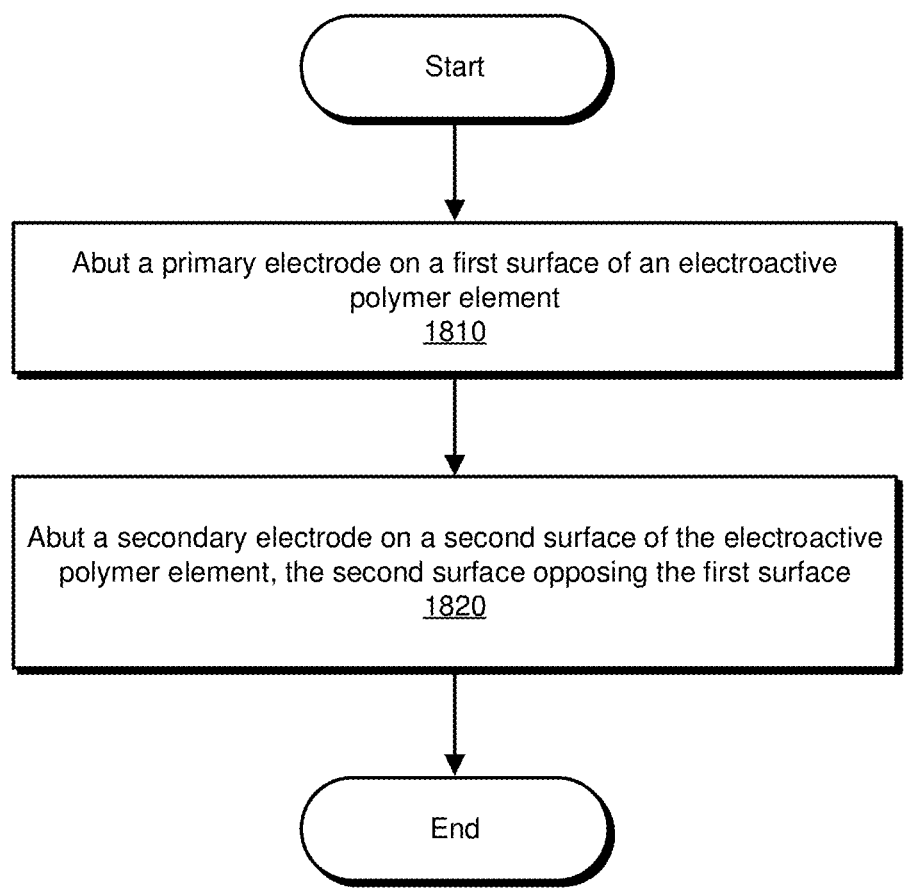
FIG. 18 is a flow chart depicting a method of manufacturing an electrostatic device in accordance with some of the embodiments.

FIG. 18 shows a flow diagram of an exemplary method 1800 for manufacturing an electroactive device, such as an electroactive actuator. As shown in FIG. 18, at step 1810, a primary electrode may be abutted on a first surface of an electroactive polymer element. For example, primary electrode 202 of FIG. 2A may be abutted (i.e., brought into contact with and/or into close proximity to) on first surface 208 of EAP element 206.

At step 1820, a secondary electrode may be abutted on a second surface of the electroactive polymer element, the second surface opposing the first surface. For example, secondary electrode 204 of FIG. 2A may be abutted on second surface 210 of EAP element 206.

In some embodiments, the electroactive polymer element may be deformable from an initial state to a deformed state in the presence of an electrostatic field produced by a potential difference between the primary electrode and the secondary electrode such that the electroactive polymer element experiences substantially uniform strain. For example, as shown in FIGS. 2A-C, EAP element 206 may be deformed from an initial state to a deformed state in the presence of an electrostatic field generated between primary electrode 202 and secondary electrode 204 such that EAP element 206 experiences substantially uniform strain. In at least one embodiment, EAP element 206 may change its state of deformation in the presence of an electrostatic field, in which this state of deformation increases the uniformity of induced strain until a maximum strain is attained.

According to some embodiments, a dielectric material may be provided between either or both of the primary and secondary electrodes. For example, a dielectric material may be applied to either the inner surface of the primary electrode or the first surface of the EAP element or both (see, e.g., FIG. 16). Similar treatment may be performed to the secondary electrode or the second surface of the EAP element or both.

According to at least one embodiment, the electroactive device may include the EAP element and one or more gaps or interstitial volumes surrounding at least a portion of the EAP element. The primary and secondary electrodes may cover, respectively, the top and bottom area of the EAP element and may extend to cover the adjoining interstitial volumes, or portions thereof. In some examples, the electroactive device may include a plurality of EAP elements and interstitial volumes arranged in an array. In various examples, the electroactive device may include multiple primary electrodes and/or multiple secondary electrodes wired together to form a common primary electrode and/or secondary electrode, or wired in any suitable manner, including individually, to provide desired or selective device control.

As discussed throughout the instant disclosure, the disclosed devices, systems, and methods may provide one or more advantages over conventional devices. For example, in contrast to prior devices, electroactive devices presented herein may include EAP elements that achieve substantially uniform strain in the presence of an electrostatic field produced by a potential difference between paired electrodes, permitting the electroactive devices to achieve, for example, improvements in both energy density and specific power density. Such uniform strain may reduce or eliminate unwanted deformations in the EAP elements and may result in greater overall deformation, such as compression, of the EAP elements, providing a greater degree of movement of surface regions of the EAP elements while requiring a lower amount of energy to provide such deformation. The EAP elements may have lateral widths that are reduced relative to their thickness, increasing the uniformity of strain and corresponding deformation. Compression of the EAP elements may be enhanced by canting side surfaces of the EAP elements and/or by arraying multiple EAP elements within the electroactive devices.

In some examples, arrayed EAP elements may be spaced with interstitial gaps or volumes that allow for transverse expansion of the EAP elements during compression, enabling multiple EAP elements having relatively reduced dimensions to be utilized simultaneously with substantially uniform strain being maintained over the arrayed EAP elements during E-field induced deformation. Such an array of EAP elements may allow for manufacturing of electroactive devices having a greater overall surface area. The arrayed EAP elements may provide substantially uniform strain and deformation throughout the electroactive devices and/or may allow for various portions of the electroactive devices to be deformed to differing degrees through the application of different potential differences to various EAP elements and/or through selection of different materials (e.g., different EAP materials) in various regions of the electroactive devices.

Electroactive devices described and shown herein may be utilized in any suitable technologies, without limitation. For example, such electroactive devices may be utilized as mechanical actuators to actuate movement of adjacent components. In at least one embodiment, the disclosed electroactive devices may be incorporated into optical systems such as adjustable lenses (e.g., fluid-filled lenses) to actuate movement of one or more optical layers. Such actuation may, for example, allow for selected movement of lens layers of an adjustable lens, resulting in deformation of the lens layers to adjust optical characteristics (e.g., focal point, spherical correction, cylindrical correction, axial correction, etc.) of the adjustable lens. In some embodiments, electroactive devices as disclosed herein may be utilized as actuators in micromechanical apparatuses, such as microelectromechanical devices. Additionally or alternatively, electroactive devices may be used for converting mechanical energy to electrical energy for use in energy harvesting systems and/or sensor apparatuses.

Embodiments of the instant disclosure may include or be implemented in conjunction with an artificial reality system. Artificial reality is a form of reality that has been adjusted in some manner before presentation to a user, which may include, e.g., a virtual reality (VR), an augmented reality (AR), a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, e.g., create content in an artificial reality and/or are otherwise used in (e.g., perform activities in) an artificial reality. The artificial reality system that provides the artificial reality content may be implemented on various platforms, including a head-mounted display (HMD) connected to a host computer system, a standalone HMD, a mobile device or computing system, or any other hardware platform capable of providing artificial reality content to one or more viewers.

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the instant disclosure. The embodiments disclosed herein should be considered in all respects illustrative and not restrictive. Reference should be made to the appended claims and their equivalents in determining the scope of the instant disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. An electroactive device comprising:
   an electroactive polymer element having a first surface and a second surface opposing the first surface;
   a primary electrode abutting the first surface; and
   a secondary electrode abutting the second surface;
   wherein the electroactive polymer element is transformed from an initial state to a deformed state and achieves substantially uniform strain by application of an electrostatic field produced by a potential difference between the primary electrode and the secondary electrode.

2. The electroactive device of claim 1, wherein the deformed state of the electroactive polymer element comprises a compressed state, wherein a direction of maximum compression of the electroactive polymer element is one substantially parallel to the electrostatic field.

3. The electroactive device of claim 1, wherein an amount of deformation of the electroactive polymer element in the deformed state corresponds to a strength of the electrostatic field.

4. The electroactive device of claim 1, wherein:
   the electroactive polymer element has a maximum thickness in an undeformed state and a minimum thickness in a maximally deformed state when an electrostatic field strength of at least a certain value is applied; and
   a ratio of the maximum thickness to the minimum thickness is from approximately 2:1 to approximately 5:1.

5. The electroactive device of claim 4, wherein a ratio of the maximum thickness to a width of the electroactive polymer element in the undeformed state is from approximately 2:1 to approximately 1:5.

6. The electroactive device of claim 4, wherein the maximum thickness of the electroactive polymer element is from approximately 100 nm to approximately 10 µm.

7. The electroactive device of claim 4, wherein a width of the electroactive polymer element in the undeformed state is from approximately 100 nm to approximately 100 µm.

8. The electroactive device of claim 1, wherein the electroactive polymer element comprises at least one of a dielectric polymer material or an elastomeric polymer material.

9. The electroactive device of claim 1, further comprising a dielectric material disposed between the electroactive polymer element and at least one of the primary electrode or the secondary electrode, wherein the dielectric material has a dielectric constant of between approximately 2 and approximately 30.

10. The electroactive device of claim 1, wherein at least one of the primary electrode or the secondary electrode comprises a movable electrode that is movable in conjunction with displacement of an abutting surface portion of the electroactive polymer element.

11. The electroactive device of claim 10, wherein:
one of the primary electrode or the secondary electrode comprises the movable electrode; and,
the other of the primary electrode or the secondary electrode comprises a fixed electrode that holds another abutting surface portion of the electroactive polymer element in a fixed position.

12. The electroactive device of claim 1, wherein:
the electroactive polymer element further comprises a third surface extending between the first surface and the second surface; and
the third surface extends at an oblique angle relative to at least one of the first surface or the second surface when the electroactive polymer element is in an undeformed state.

13. The electroactive device of claim 1, wherein:
the electroactive polymer element has a quadrilateral cross-sectional profile formed by a third surface extending between the first surface and the second surface; and
wherein an interior angle that is formed between the third surface and a direction of the electrostatic field between the primary electrode and the secondary electrode is between 0 and approximately 70 degrees when the electroactive polymer element is in an undeformed state.

14. The electroactive device of claim 1, wherein the electroactive device comprises at least one electroactive actuator.

15. The electroactive device of claim 1, wherein the electroactive polymer element is doped with barium titanate ranging in fractional composition by volume from approximately 1% to approximately 70%.

16. An electroactive device comprising:
a set of paired electrodes comprising a first set of electrodes and a second set of electrodes, each electrode of the second set of electrodes being paired with an opposing electrode of the first set of electrodes; and
an array of electroactive polymer elements separated by interstitial volumes;
wherein:
each electroactive polymer element of the array of electroactive polymer elements is disposed between the opposing electrodes of corresponding paired electrodes; and
an electrostatic field generated by each of the paired electrodes causes each electroactive polymer element disposed therebetween to deform from an initial state to a deformed state according to a strength of the electrostatic field, wherein the electrostatic field induces a substantially uniform strain in each respective electroactive polymer element.

17. The electroactive device of claim 16, wherein a first pair of opposing electrodes produces a different electrostatic field strength than a second pair of opposing electrodes.

18. The electroactive device of claim 16, wherein each electroactive polymer element of the array of electroactive polymer elements extends in an elongation direction approximately transverse to lines of an electrostatic field, wherein the elongation directions of the array of electroactive polymer elements are approximately parallel to one another.

19. The electroactive device of claim 16, wherein each of the electroactive polymer elements in the deformed state is expanded in dimensions approximately transverse to a direction of the electrostatic field between the corresponding paired electrodes to infill at least partially at least one interstitial volume.

20. A method comprising:
abutting a primary electrode on a first surface of an electroactive polymer element; and
abutting a secondary electrode on a second surface of the electroactive polymer element, the second surface opposing the first surface,
wherein the electroactive polymer element is deformable from an initial state to a deformed state in the presence of an electrostatic field produced by a potential difference between the primary electrode and the secondary electrode such that the electroactive polymer element experiences substantially uniform strain.

* * * * *